United States Patent [19]
Dixit

[11] Patent Number: 6,015,665
[45] Date of Patent: Jan. 18, 2000

[54] METHOD AND COMPOSITION FOR REGULATING APOPTOSIS

[75] Inventor: Vishva M. Dixit, Ann Arbor, Mich.

[73] Assignee: The Regents of the University of Michigan, Ann Arbor, Mich.

[21] Appl. No.: 08/389,812

[22] Filed: Feb. 13, 1995

[51] Int. Cl.$^7$ .............................. C12Q 1/68; C12N 3/00; A01N 43/04

[52] U.S. Cl. ........................... 435/6; 435/334; 435/339.1; 435/343.2; 514/44

[58] Field of Search ........................... 435/6, 334, 343.2, 435/339.1; 514/44

[56] References Cited

U.S. PATENT DOCUMENTS

| | | | |
|---|---|---|---|
| 4,107,297 | 8/1978 | Omura et al. | 424/122 |
| 4,683,195 | 7/1987 | Mullis et al. | 435/6 |
| 4,683,202 | 7/1987 | Mullis | 435/91 |
| 4,754,065 | 6/1988 | Levenson et al. | 562/564 |
| 4,800,159 | 1/1989 | Mullis et al. | 435/172.3 |
| 5,258,454 | 11/1993 | Berg et al. | 525/54.11 |
| 5,674,734 | 10/1997 | Leder et al. | 435/252.3 |

FOREIGN PATENT DOCUMENTS

| | | |
|---|---|---|
| WO 93/25685 | 12/1993 | WIPO . |
| WO 93/25694 | 12/1993 | WIPO . |
| WO 94/18317 | 8/1994 | WIPO . |
| WO 94/21817 | 9/1994 | WIPO . |
| WO 94/24297 | 10/1994 | WIPO . |
| WO 94/25621 | 11/1994 | WIPO . |
| WO 94/27583 | 12/1994 | WIPO . |
| WO 95/31544 | 11/1995 | WIPO . |
| WO 96/01642 | 1/1996 | WIPO . |
| WO 96/18641 | 6/1996 | WIPO . |
| WO 96/20721 | 7/1996 | WIPO . |
| WO 96/25945 | 8/1996 | WIPO . |
| WO 96/36698 | 11/1996 | WIPO . |
| WO 96/40713 | 12/1996 | WIPO . |
| WO 97/03998 | 2/1997 | WIPO . |
| WO 97/18313 | 5/1997 | WIPO . |
| WO 98/03648 | 1/1998 | WIPO . |

OTHER PUBLICATIONS

Tomei et al., *Apoptosis: The Molecular Basis of Cell Death* (1991) Cold Spring Harbor Press, New York. A title page and table of contents are enclosed herewith.

Tomei et al., *Apoptosis II: The Molecular Basis of Cell Death* (1994) Cold Spring Harbor Press, New York. A title page and table of contents are enclosed herewith.

Duvall et al., "Death and the cell" *Immunol. Today* (1986) 7:115–119.

Dhein et al., "Autocrine T–cell suicide mediated by APO–1/(Fas/CD95)" *Nature* (1995) 373:438–441.

Brunner et al., "Cell–autonomous Fas (CD95)/Fas–ligand interaction mediates activation–induced apoptosis in T–cell hybridomas" *Nature* (1995) 373:441–444.

Ju et al., "Fas(CD95)/FasL interactions required for programmed cell death after T–cell activation" *Nature* (1995) 373:444–448.

Spriggs et al., "Tumor necrosis factor expression in human epithelial tumor cell lines" *J. Clin. Invest.* (1988) 81:455–460.

(List continued on next page.)

*Primary Examiner*—Ponnathapura Achutamurthy
*Assistant Examiner*—Hankyel T. Park
*Attorney, Agent, or Firm*—Morrison & Foerster, LLP

[57] ABSTRACT

Methods and compositions for preventing or inhibiting apoptosis are provided by this invention. The methods require introducing into a cell which may undergo apoptosis a nucleic acid molecule coding for a gene product having crmA biological activity or a crmA polypeptide. This invention also provides compositions and methods for maintaining T cell viability in a subject infected with the human immunodeficiency virus (HIV), by administering to the subject an effective amount of a nucleic acid molecule coding for a gene product having crmA biological activity or the gene product itself.

11 Claims, 13 Drawing Sheets

OTHER PUBLICATIONS

Watanabe–Fukunaga et al., "The cDNA structure, expression, and chromosomal assignment of the mouse Fas antigen" *J. Immun.* (1992) 148:1274–1279.

Owen–Schaub et al., "Anti–Fas on onhematopoietic tumors: Levels of Fas/APO–1 and bcl–2 are not predictive of biological responsiveness" *Cancer Res.* (1994) 54:1580–1586.

Opipari, Jr. et al., "The A20 zinc finger protein protects cells from tumor necrosis factor cytotoxicity" *J. Biol. Chem.* (1992) 267:12424–12427.

Yonehara et al., "A cell–killing monoclonal antibody (ANTI–Fas) to a cell surface 21antigen co–downregulated with the receptor of tumor necrosis factor" *J. Exp. Med.* (1989) 169:1747–1756.

Pickup et al., "Hemorrhage in lesions caused by cowpox virus is induced by a viral protein that is related to plasma protein inhibitors of serine proteases" *Proc. Natl. Acad. Sci.* (1986) 83:7698–7702.

Miller et al., "Improved retroviral vectors for gene transfer and expression" *BioTechniques* (1989) 7:980–990.

Correll et al., "Production of human glucocerebrosidase in mice after retroviral gene transfer into multipotential hematopoietic progenitor cells" *Proc. Natl. Acad. Sci. USA* (1989) 86:8912–8916.

Bordignon et al., "Retroviral vector–mediated high–efficiency expression of adenosine deaminase (ADA) in hematopoietic long–term cultures of ADA–deficient marrow cells" *Proc. Natl. Acad. Sci. USA* (1989) 86:6748–6752.

Culver et al., "Lymphocytes as cellular vehicles for gene therapy in mouse and man" *Proc. Natl. Acad. Sci. USA* (1991) 88:3155–1359.

Rill et al., "An approach for the analysis of relapse and marrow reconstitution after autologous marrow transplantation using retrovirus–mediated gene transfer" *Blood* (1992) 79:2694–2700.

Anderson, "Human gene therapy" *Science* (1992) 256:808–813.

Ray et al., "Viral inhibition of inflammation: Cowpox virus encodes an inhibitor of the interleukin–1β converting enzyme" *Cell* (1992) 69:597–604.

Moss, "Poxviridae and their reproduction" *Virology*, 2nd ed., Fields, B.N. et al., eds. Raven Press, New York (1990) Chapter 74, pp. 2079–2111.

Itoh et al., "The polypeptide encoded by the cDNA for human cell surface antigen Fas can mediated apoptosis" *Cell* (1991) 66:233–243.

Laherty et al. "Human T cell leukemia virus Type I tax and phorbol 12–myristate 13–acetate induce expression of the A20 zinc finger protein by distinct mechanisms involving nuclear factor $_kB$" *J. Biol. Chem.* (1993) 268:5032–5039.

Lum et al., "Coactivation with anti–CD28 monoclonal antibody enhances anti–CD3 monoclonal antibody–induced proliferation and IL–2 synthesis in T cells from autologous bone marrow transplant recipients" *Bone Marrow Transplantation* (1993) 12:565–571.

Tartaglia et al., "A novel domain within the 55 kd TNF receptor signals cell death" *Cell* (1993) 74:845–853.

Dixit et al., "Tumor necrosis factor–α induction of novel gene products in human endothelial cells including a macrophage–specific chemotaxin" *J. Biol. Chem.* (1990) 265:2973–2978.

Barres et al., "Cell death and control of cell survival in the oligodendrocyte lineage" *Cell* (1992) 70:31–46.

Boudreau et al., "Suppression of ICE and apoptosis in mammary epithelial cells by extracellular matrix" *Science* (1995) 267:891–893.

Cerretti et al., "Molecular cloning of the interleukin–1β converting enzyme" *Science* (1992) 256:97–100.

Ellis et al., "Genetic control of programmed cell death in the nematode *C. elegans*" *Cell* (1986) 44:817–829.

Ellis et al., "Mechanisms and functions of cell death" *Ann. Rev. Cell. Biol.* (1991) 7:663–698.

Finkel et al., "Apoptosis occurs predominantly in bystander cells and not in productively infected cells of HIV– and SIV–infected lymph nodes" *Nature Med.* (1995) 1:129–134.

Gagliardini et al., "Prevention of vertebrate neuronal death by the crmA gene" *Science* (1994) 263:826–828.

Gooding, "Virus proteins that counteract host immune defenses" *Cell* (1992) 71:5–7.

Hanabuchi et al., "Fas and its ligand in a general mechanism of T–cell–mediated cytotoxicity" *Proc. Natl. Acad. Sci. USA* (1994) 91:4930–4934.

Itoh et al., "Effect of bcl–2 on Fas antigen–mediated cell death" *J. Immunol.* (1993) 151:621–627.

Itoh et al., "A novel protein domain required for apoptosis" *J. Biol. Chem.* (1993) 268:10932–10937.

Iwai et al., "Differential expression of bcl–2 and susceptibility to anti–Fas–mediated cell death in peripheral blood lymphocytes, monocytes, and neutrophils" *Blood* (1994) 84:1201–1208.

Ju et al., "Participation of target Fas protein in apoptosis pathway induced by $CD4^+$ Th1 and $CD8^+$ cytotoxic T cells" *Proc. Natl. Acad. Sci. USA* (1994) 91:4185–4189.

Kägi et al., "Fas and perforin pathways as major mechanisms of T cell–mediated cytotoxicity" *Science* (1994) 265:528–530.

King et al., "Signaling for death of lymphoid cells" *current Opinion in Immunol.* (1993) 5:368–373.

Komiyama et al., "Inhibition of interleukin–1β converting enzyme by the cowpox virus serpin CrmA" *J. Biol. Chem.* (1994) 269:19331–19337.

Kumar et al., "Protection from tumor necrosis factor–mediated cytolysis by overexpression of plasminogen activator inhibitor type–2" *J. Biol. Chem.* (1991) 266:20960–20964.

Kumar et al., "Induction of apoptosis by the mouse Nedd2 gene, which encodes a protein similar to the product of the *Caenorhabditis elegans* cell death gene ced–3 and the mammalian IL–1β–converting enzyme" *Genes & Devel.* (1994) 8:1613–1626.

Martin et al., "Biochemical characterization of programmed cell death in NGF–deprived sympathetic neurons" *J. Neurobiol.* (1992) 23:1205–1220.

Pantaleo et al., "Apoptosis in HIV Infection" *Nature Med.* (1995) 1:118–120.

Ruggiero et al., "Protection from tumor necrosis factor cytotoxicity by protease inhibitors" *Cellular Immunol.* (1987) 107:317–325.

Stalder et al., "Fas antigen is the major target nolecule for CD4+ T cell–mediated cytotoxicity" *J. Immunol.* (1994) 152:1127–1133.

Strasser, "Death of a T cell" *Nature* (1995) 373:385–387.

Suffys et al., "Involvement of a serine protease in tumour–necrosis–factor–mediated cytotoxicity" *Eur. J. Biochem.* (1988) 178:257–265.

Thornberry et al., "A novel heterodimeric cysteine protesase is required for interleukin–1β processing in monocytes" *Nature* (1992) 356:768–774.

Trauth et al., "Monoclonal antibody–mediated tumor regression by induction of apoptosis" *Science* (1989) 245:301–305.

Vaux et al., "An evolutionary perspective on apoptosis" *Cell* (1994) 76:777–779.

Walker et al., "Crystal structure of the cysteine protease interleukin–1β–converting enzyme: A (p20/p10)$_2$ homodimer" *Cell* (1994) 78:343–352.

White, "Regulation of apoptosis by the transforming genes of the DNA tumor virus adenovirus (43631)" *P.S.E.B.M.* (1993) 204:30–39.

Wilson et al., "Structure and mechanism of interleukin–1β converting enzyme" *Nature* (1994) 370:270–275.

Yuan et al., "The *C. elegans* cell death gene ced–3 encodes a protein similar to mammalian interleukin–1β–converting enzyme" *Cell* (1993) 75:641–652.

Fernandes–Alnemri et al., "CPP32, a novel human apoptotic protein with homology to *Caenorhabditis elegans* cell death protein Ced–3 and mammalian interleukin–1β–converting enzyme" *J. Biol. Chem.* (1994) 269:30761–30764.

EMBL Database, Accession #PIR P91375 Kotwal JG, Moss B. (Jan. 12, 1990) and US–A–7285510 (Jun. 20, 1989) XP002013939, 2 pages total.

EMBL Database, Accession #T10341, Sequence reference HS341, M.B. Soares et al., (Apr. 17, 1994) XP002013935, 1 page total.

Tewari et al., "Fas– and tumor necrosis factor–induced apoptosis is inhibited by the poxvirus crmA gene product" *J. Biol. Chem.* (1995) 270:3255–3260.

Tewari et al., "Yama/CPP32β, a mammalian homolog of CED–3, is a CrmA–inhibitable protease that cleaves the death substrate poly(ADP–Ribose)polymerase" *Cell* (1995) 81:801–809.

Nicholson et al., "Identification and inhibition of the ICE/CED–3 protease necessary for mammalian apoptosis" *Nature* (1995) 376:37–43.

Rathmell et al. "Expansion or Elimination of B Cells In Vivo: Dual Roles for CD40– and Fas (CD95)–Ligands Modulated by the B Cell Antigen Receptor" *Cell* (1996) 87:319–329.

Strand et al. "Lymphocyte apoptosis induced by CD95 (APO–1/Fas) ligand–expressing tumor cells—A mechanism of immune evasion?" *Nature Medicine* (1996) 2(12):1361–1366.

Tewari et al. "CrmA, a poxvirus–encoded serpin, inhibits cytotoxic T–lymphocyte–mediated apoptosis" *J. Biol. Chem.* (1995) 270(39):22705–22708.

Gagliardini et al. Science, 263:826–828, 1994.

Ray et al., Cell, 69:597–604, 1992.

Marshall et al. "Sequence and Functional Expression of a single α subunit of an insect nicotinic acetylcholine receptor" *The EMBO Jrnl.* 9(13):4391–98 (1990).

Allison et al., "The yin and yang of T cell costimulation" *Science* (1995) 270:932–933.

Baglioni "Mechanisms of cytotoxicity, cytolysis, and growth stimulation by TNF" *Tumor Necrosis Factor. The Molecules and Their Emerging Role in Medicine* (1992) B. Beutler, M.D., etd., Raven Press, New York. A title page and table of contents are enclosed herewith.

Beidler et al., "The baculovirus p35 protein inhibits fas– and tumor necrosis factor–induced apoptosis" *J. Biol. Chem.* (1995) 270:16526–16528.

Blau et al., "Molecular medicine: Gene therapy—a novel form of drug delivery" *N. Eng. J. Med.* (1995) 333:1204–1207.

Boldin et al., "A novel protein that interacts with the death domain of Fas/APO1 contains a sequence motif related to the death domain" *J. Biol. Chem.* (1995) 270:7795–7798.

Boldin et al., "Self–association of the 'death domains' of the p55 tumor necrosis factor (TNF) receptor and Fas/APO1 prompts signaling for TNF and Fas/APO1 effects" *J. Biol. Chem.* (1995) 270:387–391

Bose et al., "Ceramide synthase mediates daunorubicin–induced apoptosis: An alternative mechanism for generating death signals" *Cell* (1995) 82:405–414.

Boulakia et al., "Bcl–2 and adenovirus E1B 19 kDa protein prevent E1A–induced processing of CPP32 and cleavage of poly(ADP–ribose) polymerase" *Oncogene* (1996) 12:529–535.

Bump et al., "Inhibition of ICE family proteases by baculovirus antiapopototic protein p35" *Science* (1995) 269:1885–1888.

Casciola–Rosen et al., "Specific cleavage of the 70–kDa protein component of the U1 small nuclear ribonucleoprotein is a characteristic biochemical feature of apoptotic cell death" *J. Biol. Chem.* (1994) 269:30757–30760.

Chinnaiyan et al., "FADD/MORT1 is a common mediator of CD95 (Fas/APO–1) and tumor necrosis factor receptor–induced apoptosis" *J. Biol. Chem.* (1996) 271:4961–4965.

Chinnaiyan et al., "Molecular ordering of the cell death pathway" *J. Biol. Chem.* (1996) 271:4573–4576.

Chinnaiyan et al., "FADD, a novel death domain–containing protein, interacts with the death domain of Fas and initiates apoptosis" *Cell* (1995) 81:505–512.

Clem et al., "Prevention of apoptosis by a baculovirus gene during infection of insect cells" *Science* (1991) 254:1388–1390.

Clem et al., "Control of programmed cell death by the baculovirus genes p35 and iap" *Mol. & Cell. Biol.* (1994) 14:5212–5222.

Clement et al., "Fas and tumor necrosis factor receptor–mediated cell death: Similarities and distinctions" *J. Exp. Med.* (1994) 180:557–567.

Cleveland et al., "Contenders in FasL/TNF death signaling" *Cell* (1995) 81:479–482.

Cohen, "Apoptosis" *Immunology Today* (1993) 14:126–130.

Darmon et al., "Activation of the apoptotic protease CPP32 by cytotoxic T–cell–derived granzyme B" *Nature* (1995) 377:446–448.

Duan et al., "ICE–LAP3, a novel mammalian homologue of the *Caenorhabditis elegans* cell death protein CED–3 is activated during Fas– and tumor necrosis factor–induced apoptosis" *J. Biol. Chem.* (1996) 271:1621–1625.

Faucheu et al., "A novel human protease similar to the interleukin–1β converting enzyme induces apoptosis in transfected cells" *EMBO J.* (1995) 14:1914–1922.

Fernandes–Alnemri et al., "Mch2, a new member of the apoptotic Ced–3/Ice cysteine protease gene family" *Cancer Res.* (1995) 55:2737–2742.

Fernandes–Alnemri et al., "Mch3, a novel human apoptotic cysteine protease highly related to CPP32" *Cance Res.* (1995) 55:6045–6052.

Fisher et al., "Dominant interfering Fas gene mutations impair apoptosis in a human autoimmune lymphoproliferative syndrome" *Cell* (1995) 81:935–946.

Golstein et al., "Homology between reaper and the cell death domains of Fas and TNFR1" *Cell* (1995) 81:185–186.

Harper et al., "The p21 Cdk–interacting protein Cip1 is a potent inhibitor of G1 cyclin–dependent kinases" *Cell* (1993) 75:805–816.

Henderson et al., "Epstein–Barr virus–coded BHRF1 protein, a viral homologue of Bcl–2, protects human B cells from programmed cell death" Proc. Natl. Acad. Sci. USA (1993) 90:8479–8483.

Hengartner, "Life and death decisions: ced–9 and programmed cell death in Caenorhabditis elegans" Science (1995) 270:931.

Herlyn et al., "Anti–idiotypic antibodies bear the internal image of a human tumor antigen" Science (1986) 232:100–102.

Higuchi et al., "A general method of in vitro preparation and specific mutagenesis of DNA fragments: study of protein and DNA interactions" Nucleic Acids Res. (1988) 16:7351–7367.

Hsu et al., "The TNF receptor 1–associated protein TRADD signals cell death and NF–kB activation" Cell (1995) 81:495–504.

Hsu et al., "TRADD–TRAF2 and TRADD–FADD interactions define two distinct TNF receptor 1 signal transduction pathways" Cell (1996) 84:299–308.

Hu et al., "A novel RING finger protein interacts with the cytoplasmic domain of CD40" J. Biol. Chem. (1994) 269:30069–30072.

Hynes et al., "A target for tumour–directed therapy" Nature Medicine (1995) 1:631–632.

Kamens et al., "Identification and characterization of ICH–2, a novel member of the interleukin–1β–converting enzyme family of cysteine proteases" J. Biol. Chem. (1995) 270:15250–15256.

Kaufmann et al., "Specific proteolytic cleavage of poly(ADP–ribose) polymerase: An early marker of chemotherapy–induced apoptosis" Cancer Research (1993) 53;3976–3985.

Kischkel et al., "Cytotoxicity–dependent APO–1 (Fas/CD95)–associated proteins form a death–inducing signaling complex (DISC) with the receptor" EMBO J. (1995) 14:5579–5588.

Kuida et al., "Altered cytokine export and apoptosis in mice deficient in interleukin–1β converting enzyme" Science (1995) 267:2000–2003.

Kuby, "Immunology" W.H. Freeman and Company, N.Y. (1992) 257.

Lazebnik et al., "Cleavage of poly(ADP–ribose) polymerase by a proteinase with properties like ICE" Nature (1994) 371:346–347.

Li et al., "Mice deficient in IL–1β–converting enzyme are defective in production of mature IL–1β and resistant to endotoxic shock" Cell (1995) 80:401–411.

Liston et al., "Suppression of apoptosis in mammalian cells by NAIP and a related family of IAP genes" Nature (1996) 379:349–353.

Maekawa et al. "Molecular cloning of a novel protein–tyrosine phosphatase containing a membrane–binding domain and GLGF repeats" FEBS Letters 337 (1994) 200–206.

Margolick et al., "Failure of T–cell homeostatis preceding AIDS in HIV–1 infection" Nature Medicine (1995) 1:674–680.

Martinou et al., "Viral proteins E1B19K and p35 protect sympathetic neurons from cell death induced by NGF deprivation" J. Cell Biol. (1995) 128:201–208.

McElvaney et al., "IL–6 release and airway administration of human CFTR cDNA adenovirus vector" Nature Medicine (1995) 1:182–184.

Milner, "DNA damage, p53 and anticancer therapies" Nature Medicine (1995) 1:879–880.

Miura et al., "Induction of apoptosis in fibroblasts by IL–1β–converting enzyme, a mammalian homolog of the C. elegans cell death gene ced–3" Cell (1993) 75:653–660.

Morrison, et al. "Direct Activation of the Serine/Threonine Kinase Activity of Raf/1 through Tyrosine Phosphorylation by the PDGF β–Receptor" Cell (1989) 58:649–57.

Munday et al., "Molecular cloning and pro–apoptotic activity of $ECE_{rel}II$ and $ICE_{rel}III$, members of the ICE/CED–3 family of cysteine proteases" J. Biol. Chem. (1995) 270:15870–15876.

Na et al., "D4–GDI, a substrate of CPP32, is proteolyzed during Fas–induced apoptosis" J. Biol. Chem. (1996) 271:11209–11213.

Nicholson, "ICE/CED3–like proteases as therapeutic targets for the control of inappropriate apoptosis" Nature Biotechnol. (1996) 14:297–301.

O'Rourke et al., "Thrombospondin 1 and thrombospondin 2 are expressed as both homo– and heterotimers" J. Biol. Chem. (1992) 267:24921–24924.

Oi et al., "Chimeric antibodies" Bio/Techniques (1986) 4:214–221.

Orkin, et al. "Report and recommendation of the panel to assess the NIH investment in research on gene therapy" (1995).

Paigen, "A miracle enough: the power of mice" Nature Medicine (1995) 1:215–220.

Peter et al., "CD95 (APO–1/FAS)–associating signalling proteins" Cell Death and Differentiation (1996) 3:161–170.

Peters et al., "Ankyrins: Structure and function in normal cells and hereditary spherocytes" Seminars in Hematol. (1993) 30:85–118.

Rabizadeh et al., "Expression of the baculovirus p35 gene inhibits mammalian neural cell death" J. Neurochem. (1993) 61:2318–2321.

Roederer, "T–cell dynamics of immunodeficiency" Nature Medicine (1995) 1:621–622.

Ron et al., "pGSTag—A versatile bacterial expression plasmid for enzymatic labeling of recombinant proteins" Bio/Techniques (1992) 13:866–869.

Rothe et al., "TRAF2–mediated activation of NF–kB by TNF receptor 2 and CD40" Science (1995) 269:1424–1427.

Rothe et al., "The TNFR2–TRAF signaling complex contains two novel proteins related by baculoviral inhibitor of apoptosis proteins" Cell (1995) 83:143–1452.

Roy et al., "The gene for neuronal apoptosis inhibitory protein is partially deleted in individuals with spinal muscular atrophy" Cell (1995) 80:167–178.

Schlegel et al., "CPP32/apopain is a key interleukin 1β converting enzyme–like protease involved in Fas–mediated apoptosis" J. Biol. Chem. (1996) 271:1841–1844.

Smith et al., "CrmA expression in T lymphocytes of transgenic mice inhibits CD95 (Fas/APO–1)–transduced apoptosis, but does not cause lymphadenopathy or autoimmune disease" The EMBO Journal, 15(19):5167–5176 (1996).

Song, "Aggregation of the intracellular domain of the Type 1 tumor necrosis factor receptor defined by the two–hybrid system" J. Biol. Chem. (1994) 269:22492–22495.

Spira et al., "The identification of monoclonal class switch variatns by sib selection and an ELISA assay" J. Immunol. Meth. (1984) 74:307–315.

Stanger et al., "RIP: A novel protein containing a death domain that interacts with Fas/APO–1 (CD95) in yeast and causes cell death" Cell (1995) 81:513–523.

Steplewski et al., "Isolation and characterization of anti–monosialoganglioside monoclonal antibody 19–9 class–switch variants" *Proc. Natl. Acad. Sci. USA* (1985) 82:8653–8657.

Stinchcomb, "Constraining the cell cycle: Regulating cell division and differentiation by gene therapy" *Nature Medicine* (1995) 1:1004–1006.

Studier, "Use of bacteriophage T7 lysozyme to improve an inducible T7 expression system" *J. Mol. Biol.* (1991) 219:37–44.

Sugimoto et al., "Baculovirus p35 prevents developmentally programmed cell death and rescues a ced–9 mutant in the nematode *Caenorhabditis elegans*" *EMBO J.* (1994) 13:2023–2028.

Tamura et al., "An IRF–1–dependent pathway of DNA damage–induced apoptosis in mitogen–activated T lymphocytes" *Nature* (1995) 376:596–599.

Tanaka et al., "Fas ligand in human serum" *Nature Medicine* (1996) 2;317–322.

Tartaglia et al., "Two TNF receptors" *Immunol. Today* (1992) 13:151–153.

Tewari et al., "CrmA–inhibitable cleavage of the 70–kDa protein component of the U1 small nuclear ribonucleoprotein during Fas– and tumor necrosis factor–induced apoptosis" *J. Biol. Chem.* (1995) 270:18738–18741.

vanBockxmeer et al., "Premature ischaemic heart disease and the gene for coagulation factor V" *Nature Medicine* (1995) 1:185.

Verheji et al., "Requirement for ceramide–initiated SAPK/JNK signalling in stress–induced apoptosis" *Nature* (1996) 380:75–79.

Vermes et al., "Apoptosis and programmed cell death in health and disease" (1994) Academic Press, Inc., pp. 177–246.

Vito et al., "Interfering witih apoptosis: $Ca^{2+}$–binding protein ALG–2 and Alzheimer's disease gene ALG–3" *Science* (1996) 271:521–525.

Wang et al., "Ich–1, an Ice/ced–3–related gene, encodes both positive and negative regulators of programmed cell death" *Cell* (1994) 78:739–750.

Wang et al., "Cleavage of sterol regulatory element binding proteins (SREBPs) by CPP32 durin apoptosis" *EMBO J.* (1996) 15:1012–1020.

Watanabe–Fukunaga et al., "Lymphoproliferation disorder in mice explained by defects in Fas antigen that mediates apoptosis" *Nature* (1992) 356:314–317.

Westendorp et al., "Sensitization of T cells to CP95–mediated apoptosis by HIV–1 Tat and gp120" *Nature* (1995) 375:497–503.

Whyte et al., "The last cut is the deepest" *Nature* (1995) 376: 17–18.

Williams et al., "Apoptotic cell death induced by intracellular proteolysis" *J. Immunol.* (1994) pp. 4247–4255.

Woo, "Apoptosis and loss of renal tissue in polycystic kidney diseases" *N. Eng. J. Med.* (1995) 333:18–25.

Wu et al., "Interaction of the erythropoietin and stem–cell–factor receptors" *Nature* (1995) 377:242–246.

Xue et al., "Inhibition of the *Caenorhabditis elegans* cell–death protease CED–3 by a CED–3 cleavage site in baculovirus p35 protein" *Nature* (1995) 377:248–251.

Zheng et al. "Induction of apoptosis in mature T cells by tumour necrosis factor" *Nature* (1995) 377:348–351.

Chinnaiyan et al. "Signal Transduction by DR3, a Death Domain–Containing Receptor Related to TNFR–1 and CD95" *Science* (1996) 274:990–992.

Hu et al. "A Novel Family of Viral Death Effector Domain–containing Molecules that Inhibit Both CD–95– and Tumor Necrosis Factor Receptor–1–induced Apoptosis" *J. Biol. Chem.* (1997) 272:9621–9624.

Pan et al. "The Receptor for the Cytotoxic Ligand TRAIL" *Science* (1997) 276:111–113.

Daniel et al. (1994) "Mapping of linear antigenic sites on the S glycoprotein of a nuurotropic murine coronavirus with synthetic peptides: a combination of nine prediction algorithms fails to identify relevant epitopes and peptide immunogenicity is drastically influenced by the nature of the protein carrier" *Virology* 202:549–9.

Tewari et al. (1995) CrmA, a poxvirus–encoded serpin, inhibits cytotoxic T–lymphocyte–mediated apoptosis *J. Biol. Chem.* 270(39):22705–22708.

```
              10        20        30        40        50        60
     TCCATGGAAGAACGAAAGTAGTATAAAAGTAATAAAACAAAAAAAAGAATATAAAAAATT 70        80        90       100       110       120
     TATAGCCACTTTCTTTGAGGACTGTTTTCCTGAAGGAAATGAACCTCTGGAATTAGTTAG 130       140       150       160       170       180
     ATATATAGAATTAGTATACACGCTAGATTATTCTCAAACTCCTAATTATGACAGACTACG 190       200       210       220       230       240
     TAGACTGTTTATACAAGATTGAAAATATATTTCTTTTTATTGAGTGGTGGTAGTTACGGA 250       260       270       280       290       300
     TATCTAATATTAATATTAGACTATCTCTATCGTCACACAACAAAATCGATTGCCATGGAT
                                                             M  D 310       320       330       340       350       360
     ATCTTCAGGGAAATCGCATCTTCTATGAAAGGAGAGAATGTATTCATTTCTCCACCGTCA
      I  F  R  E  I  A  S  S  M  K  G  E  N  V  F  I  S  P  P  S 370       380       390       400       410       420
     ATCTCGTCAGTATTGACAATACTGTATTATGGAGCTAATGGATCCACTGCTGAACAGCTA
      I  S  S  V  L  T  I  L  Y  Y  G  A  N  G  S  T  A  E  Q  L 430       440       450       460       470       480
     TCAAAATATGTAGAAAAGGAGGCGGACAAGAATAAGGATGATATCTCATTCAAGTCCATG
      S  K  Y  V  E  K  E  A  D  K  N  K  D  D  I  S  F  K  S  M 490       500       510       520       530       540
     AATAAAGTATATGGGCGATATTCTGCAGTGTTTAAAGATTCCTTTTTGAGAAAAATTGGA
      N  K  V  Y  G  R  Y  S  A  V  F  K  D  S  F  L  R  K  I  G 550       560       570       580       590       600
     GATAATTTCCAAACTGTTGACTTCACTGATTGTCGCACTGTAGATGCGATCAACAAGTGT
      D  N  F  Q  T  V  D  F  T  D  C  R  T  V  D  A  I  N  K  C 610       620       630       640       650       660
     GTTGATATCTTCACTGAGGGGAAAATTAATCCACTATTGGATGAACCATTGTCTCCAGAT
      V  D  I  F  T  E  G  K  I  N  P  L  L  D  E  P  L  S  P  D 670       680       690       700       710       720
     ACCTGTCTCCTAGCAATTAGTGCCGTATACTTTAAAGCAAAATGGTTGATGCCATTTGAA
      T  C  L  L  A  I  S  A  V  Y  F  K  A  K  W  L  M  P  F  E
```

FIG. 5A

```
     730       740       750       760       770       780
AAGGAATTTACCAGTGATTATCCCTTTTACGTATCTCCAACGGAAATGGTAGATGTAAGT
 K  E  F  T  S  D  Y  P  F  Y  V  S  P  T  E  M  V  D  V  S 790       800       810       820       830       840
ATGATGTCTATGTACGGCGAGGCATTTAATCACGCATCTGTAAAAGAATCATTCGGCAAC
 M  M  S  M  Y  G  E  A  F  N  H  A  S  V  K  E  S  F  G  N 850       860       870       880       890       900
TTTTCAATCATAGAACTGCCATATGTTGGAGATACTAGTATGGTGGTAATTCTTCCAGAC
 F  S  I  I  E  L  P  Y  V  G  D  T  S  M  V  V  I  L  P  D 910       920       930       940       950       960
AATATTGATGGACTAGAATCCATAGAACAAAATCTAACAGATACAAATTTTAAGAAATGG
 N  I  D  G  L  E  S  I  E  Q  N  L  T  D  T  N  F  K  K  W 970       980       990      1000      1010      1020
TGTGACTCTATGGATGCTATGTTTATCGATGTGCACATTCCCAAGTTTAAGGTAACAGGC
 C  D  S  M  D  A  M  F  I  D  V  H  I  P  K  F  K  V  T  G 1030      1040      1050      1060      1070      1080
TCGTATAATCTGGTGGATGCGCTAGTAAAGTTGGGACTGACAGAGGTGTTCGGTTCAACT
 S  Y  N  L  V  D  A  L  V  K  L  G  L  T  E  V  F  G  S  T 1090      1100      1110      1120      1130      1140
GGAGATTATAGCAATATGTGTAATTCAGATGTGAGTGTCGACGCTATGATCCACAAAACG
 G  D  Y  S  N  M  C  N  S  D  V  S  V  D  A  M  I  H  K  T 1150      1160      1170      1180      1190      1200
TATATAGATGTCAATGAAGAGTATACAGAAGCAGCTGCAGCAACTTGTGCGCTGTTGGCA
 Y  I  D  V  N  E  E  Y  T  E  A  A  A  A  T  C  A  L  V  A 1210      1220      1230      1240      1250      1260
GACTGTGCATCAACAGTTACAAATGAGTTCTGTGCAGATCATCCGTTCATCTATGTGATT
 D  C  A  S  T  V  T  N  E  F  C  A  D  H  P  F  I  Y  V  I 1270      1280      1290      1300      1310      1320
AGGCATGTCGATGGCAAAATTCTTTTCGTTGGTAGATATTGCTCTCCAACAACTAATTAA
 R  H  V  D  G  K  I  L  F  V  G  R  Y  C  S  P  T  T  N  *

1330      1340      1350      1360      1370      1380
ATCACATTCTTAATATTAGAATATTAGAATATTATATAGTTAAGATTTTTACTAATTGGT
```

FIG. 5B

```
      1390      1400      1410      1420      1430      1440
TAACCATTTTTTTAAAAAAATAGAAAAAAAACATGTTATATTAGCGAGGGTCGTTATTCT 1450      1460
TCCAATTGCAATTGGTAAGATGACGGCC
```

FIG. 5C

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (xi) SEQUENCE DESCRIPTION: SEQ ID NO:1:

CACCGGAATT CCACCATGGA TATCTTCAGG GAAATCG                                37

(2) INFORMATION FOR SEQ ID NO:2:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (xi) SEQUENCE DESCRIPTION: SEQ ID NO:2:

GCTCTAGACT CGAGTTAATT AGTTGTTGGA GAGCAATATC                             40

(2) INFORMATION FOR SEQ ID NO:3:

(i) SEQUENCE CHARACTERISTICS:
      (A) LENGTH: 1468 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 295..1317

(xi) SEQUENCE DESCRIPTION: SEQ ID NO:3:

```
TCCATGGAAG AACGAAAGTA GTATAAAAGT AATAAAACAA AAAAAAGAAT ATAAAAAATT            60

TATAGCCACT TTCTTTGAGG ACTGTTTTCC TGAAGGAAAT GAACCTCTGG AATTAGTTAG           120

ATATATAGAA TTAGTATACA CGCTAGATTA TTCTCAAACT CCTAATTATG ACAGACTACG           180

TAGACTGTTT ATACAAGATT GAAAATATAT TTCTTTTTAT TGAGTGGTGG TAGTTACGGA           240

TATCTAATAT TAATATTAGA CTATCTCTAT CGTCACACAA CAAAATCGAT TGCC ATG            297
                                                          Met
                                                           1

GAT ATC TTC AGG GAA ATC GCA TCT TCT ATG AAA GGA GAG AAT GTA TTC            345
Asp Ile Phe Arg Glu Ile Ala Ser Ser Met Lys Gly Glu Asn Val Phe
            5                  10                  15

ATT TCT CCA CCG TCA ATC TCG TCA GTA TTG ACA ATA CTG TAT TAT GGA            393
Ile Ser Pro Pro Ser Ile Ser Ser Val Leu Thr Ile Leu Tyr Tyr Gly
        20                  25                  30

GCT AAT GGA TCC ACT GCT GAA CAG CTA TCA AAA TAT GTA GAA AAG GAG            441
Ala Asn Gly Ser Thr Ala Glu Gln Leu Ser Lys Tyr Val Glu Lys Glu
    35                  40                  45

GCG GAC AAG AAT AAG GAT GAT ATC TCA TTC AAG TCC ATG AAT AAA GTA            489
Ala Asp Lys Asn Lys Asp Asp Ile Ser Phe Lys Ser Met Asn Lys Val
50                  55                  60                  65

TAT GGG CGA TAT TCT GCA GTG TTT AAA GAT TCC TTT TTG AGA AAA ATT            537
Tyr Gly Arg Tyr Ser Ala Val Phe Lys Asp Ser Phe Leu Arg Lys Ile
                70                  75                  80
```

-continued

```
GGA GAT AAT TTC CAA ACT GTT GAC TTC ACT GAT TGT CGC ACT GTA GAT        585
Gly Asp Asn Phe Gln Thr Val Asp Phe Thr Asp Cys Arg Thr Val Asp
             85                  90                  95

GCG ATC AAC AAG TGT GTT GAT ATC TTC ACT GAG GGG AAA ATT AAT CCA        633
Ala Ile Asn Lys Cys Val Asp Ile Phe Thr Glu Gly Lys Ile Asn Pro
    100                 105                 110

CTA TTG GAT GAA CCA TTG TCT CCA GAT ACC TGT CTC CTA GCA ATT AGT        681
Leu Leu Asp Glu Pro Leu Ser Pro Asp Thr Cys Leu Leu Ala Ile Ser
115                 120                 125

GCC GTA TAC TTT AAA GCA AAA TGG TTG ATG CCA TTT GAA AAG GAA TTT        729
Ala Val Tyr Phe Lys Ala Lys Trp Leu Met Pro Phe Glu Lys Glu Phe
130                 135                 140                 145

ACC AGT GAT TAT CCC TTT TAC GTA TCT CCA ACG GAA ATG GTA GAT GTA        777
Thr Ser Asp Tyr Pro Phe Tyr Val Ser Pro Thr Glu Met Val Asp Val
             150                 155                 160

AGT ATG ATG TCT ATG TAC GGC GAG GCA TTT AAT CAC GCA TCT GTA AAA        825
Ser Met Met Ser Met Tyr Gly Glu Ala Phe Asn His Ala Ser Val Lys
                 165                 170                 175

GAA TCA TTC GGC AAC TTT TCA ATC ATA GAA CTG CCA TAT GTT GGA GAT        873
Glu Ser Phe Gly Asn Phe Ser Ile Ile Glu Leu Pro Tyr Val Gly Asp
        180                 185                 190

ACT AGT ATG GTG GTA ATT CTT CCA GAC AAT ATT GAT GGA CTA GAA TCC        921
Thr Ser Met Val Val Ile Leu Pro Asp Asn Ile Asp Gly Leu Glu Ser
    195                 200                 205

ATA GAA CAA AAT CTA ACA GAT ACA AAT TTT AAG AAA TGG TGT GAC TCT        969
Ile Glu Gln Asn Leu Thr Asp Thr Asn Phe Lys Lys Trp Cys Asp Ser
210                 215                 220                 225

ATG GAT GCT ATG TTT ATC GAT GTG CAC ATT CCC AAG TTT AAG GTA ACA       1017
Met Asp Ala Met Phe Ile Asp Val His Ile Pro Lys Phe Lys Val Thr
             230                 235                 240

GGC TCG TAT AAT CTG GTG GAT GCG CTA GTA AAG TTG GGA CTG ACA GAG       1065
Gly Ser Tyr Asn Leu Val Asp Ala Leu Val Lys Leu Gly Leu Thr Glu
                 245                 250                 255

GTG TTC GGT TCA ACT GGA GAT TAT AGC AAT ATG TGT AAT TCA GAT GTG       1113
Val Phe Gly Ser Thr Gly Asp Tyr Ser Asn Met Cys Asn Ser Asp Val
        260                 265                 270

AGT GTC GAC GCT ATG ATC CAC AAA ACG TAT ATA GAT GTC AAT GAA GAG       1161
Ser Val Asp Ala Met Ile His Lys Thr Tyr Ile Asp Val Asn Glu Glu
    275                 280                 285

TAT ACA GAA GCA GCT GCA GCA ACT TGT GCG CTG GTG GCA GAC TGT GCA       1209
Tyr Thr Glu Ala Ala Ala Ala Thr Cys Ala Leu Val Ala Asp Cys Ala
290                 295                 300                 305

TCA ACA GTT ACA AAT GAG TTC TGT GCA GAT CAT CCG TTC ATC TAT GTG       1257
Ser Thr Val Thr Asn Glu Phe Cys Ala Asp His Pro Phe Ile Tyr Val
             310                 315                 320

ATT AGG CAT GTC GAT GGC AAA ATT CTT TTC GTT GGT AGA TAT TGC TCT       1305
Ile Arg His Val Asp Gly Lys Ile Leu Phe Val Gly Arg Tyr Cys Ser
                 325                 330                 335

CCA ACA ACT AAT TAAATCACAT TCTTAATATT AGAATATTAG AATATTATAT           1357
Pro Thr Thr Asn
            340

AGTTAAGATT TTTACTAATT GGTTAACCAT TTTTTTAAAA AAATAGAAAA AAAACATGTT     1417

ATATTAGCGA GGGTCGTTAT TCTTCCAATT GCAATTGGTA AGATGACGGC C              1468
```

(2) INFORMATION FOR SEQ ID NO:4:

(i) SEQUENCE CHARACTERISTICS:
        (A) LENGTH: 341 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Ile Phe Arg Glu Ile Ala Ser Ser Met Lys Gly Glu Asn Val
 1               5                  10                  15

Phe Ile Ser Pro Pro Ser Ile Ser Ser Val Leu Thr Ile Leu Tyr Tyr
                20                  25                  30

Gly Ala Asn Gly Ser Thr Ala Glu Gln Leu Ser Lys Tyr Val Glu Lys
            35                  40                  45

Glu Ala Asp Lys Asn Lys Asp Asp Ile Ser Phe Lys Ser Met Asn Lys
    50                  55                  60

Val Tyr Gly Arg Tyr Ser Ala Val Phe Lys Asp Ser Phe Leu Arg Lys
65                  70                  75                  80

Ile Gly Asp Asn Phe Gln Thr Val Asp Phe Thr Asp Cys Arg Thr Val
                85                  90                  95

Asp Ala Ile Asn Lys Cys Val Asp Ile Phe Thr Glu Gly Lys Ile Asn
                100                 105                 110

Pro Leu Leu Asp Glu Pro Leu Ser Pro Asp Thr Cys Leu Leu Ala Ile
            115                 120                 125

Ser Ala Val Tyr Phe Lys Ala Lys Trp Leu Met Pro Phe Glu Lys Glu
    130                 135                 140

Phe Thr Ser Asp Tyr Pro Phe Tyr Val Ser Pro Thr Glu Met Val Asp
145                 150                 155                 160

Val Ser Met Met Ser Met Tyr Gly Glu Ala Phe Asn His Ala Ser Val
                165                 170                 175

Lys Glu Ser Phe Gly Asn Phe Ser Ile Ile Glu Leu Pro Tyr Val Gly
            180                 185                 190

Asp Thr Ser Met Val Val Ile Leu Pro Asp Asn Ile Asp Gly Leu Glu
    195                 200                 205

Ser Ile Glu Gln Asn Leu Thr Asp Thr Asn Phe Lys Lys Trp Cys Asp
    210                 215                 220

Ser Met Asp Ala Met Phe Ile Asp Val His Ile Pro Lys Phe Lys Val
225                 230                 235                 240

Thr Gly Ser Tyr Asn Leu Val Asp Ala Leu Val Lys Leu Gly Leu Thr
                245                 250                 255

Glu Val Phe Gly Ser Thr Gly Asp Tyr Ser Asn Met Cys Asn Ser Asp
            260                 265                 270

Val Ser Val Asp Ala Met Ile His Lys Thr Tyr Ile Asp Val Asn Glu
    275                 280                 285

Glu Tyr Thr Glu Ala Ala Ala Thr Cys Ala Leu Val Ala Asp Cys
290                 295                 300

Ala Ser Thr Val Thr Asn Glu Phe Cys Ala Asp His Pro Phe Ile Tyr
305                 310                 315                 320

Val Ile Arg His Val Asp Gly Lys Ile Leu Phe Val Gly Arg Tyr Cys
                325                 330                 335

Ser Pro Thr Thr Asn
            340
```

METHOD AND COMPOSITION FOR REGULATING APOPTOSIS

This invention was made in part with Government support under Grant No. CA61348 awarded from the National Institute of Health. The U.S. government has certain rights in this invention.

FIELD OF THE INVENTION

This invention relates to methods for regulating apoptosis in a population of cells as well as compositions useful to regulate apoptosis.

BACKGROUND OF THE INVENTION

Apoptosis, or programmed cell death (PCD) is a type of cell death that is fundamentally distinct from degenerative death or necrosis. It is an active process of gene-directed cellular self-destruction which in some instances, serves a biologically meaningful homeostatic function. This can be contrasted to necrosis which is cell death occurring as the result of severe injurious changes in the environment of infected cells. For a general review of apoptosis, see Tomei, L. D. and Cope, F. O. *Asoptosis: The Molecular Basis of Cell Death* (1991) Cold Spring Harbor Press, N.Y.; Tomei, L. D. and Cope, F. O. *Apoptosis II: The Molecular Basis of Apoptosis in Disease* (1994) Cold Spring Harbor Press, N.Y.; and Duvall and Wyllie (1986) *Immun. Today* 7(4):115–119.

Morphologically, apoptosis is characterized by the rapid condensation of the cell with preservation of membranes. Synchronistically with the compaction of chromatin, several biochemical changes occur in the cell. Nuclear DNA is cleaved at the linker regions between nucleosomes to produce fragments which are easily demonstrated by agarose gel electrophoresis wherein a characteristic ladder develops.

Apoptosis has been linked to many biological processes, including embryogenesis, development of the immune system, elimination of virus-infected cells, and the maintenance of tissue homeostasis. Apoptosis also occurs as a result of human immunodeficiency virus (HIV) infection of CD4+ T lymphocytes (T cells). Indeed, one of the major characteristics of AIDS is the gradual depletion of CD4+ T lymphocytes during the development of the disease. Several mechanisms, including apoptosis, have been suggested to be responsible for the CD4 depletion. It is speculated that apoptotic mechanisms might be mediated either directly or by the virus replication as a consequence of the HIV envelope gene expression, or indirectly by priming uninfected cells to apoptosis when triggered by different agents.

The depletion of CD4+ T cells results in the impairment of the cellular immune response. It has been proposed that an inappropriate activation-induced T cell PCD causes the functional and numerical abnormalities of $T_H$ cells from HIV-infected patients, that leads to the near collapse of the patient's immune system.

Therefore, it is advantageous to block apoptosis and the ensuing depletion of T cells. Accordingly, a need exists to maintain T cell function and viability in HIV infected individuals and to provide systems to screen for new drugs that may assist in maintaining the cellular immune response. This invention satisfies this need and provides related advantages as well.

SUMMARY OF THE INVENTION

This invention provides compositions and methods for preventing or inhibiting apoptosis in a suitable cell by introducing into the cell a nucleic acid molecule coding for a gene product having crmA biological activity or alternatively, the crmA gene product.

Also provided by this invention are compositions and methods for preventing or inhibiting induced apoptosis in a suitable cell by introducing into the cell a nucleic acid molecule coding for a gene product having cytokine response modifier crmA biological activity or the gene product so that induced apoptosis is prevented or inhibited.

Further provided by this invention are compositions and methods for maintaining T cell viability in a subject infected with or susceptible to infection with the human immunodeficiency virus by administering to the subject an effective amount of a nucleic acid molecule coding for a gene product having crmA biological activity or the crmA gene product.

BRIEF DESCRIPTION OF THE FIGURES

FIG. 3B top: Northern analysis of corresponding cell lines to detect crmA transcript. FIG. 3B bottom: Northern analysis to detect β-actin transcript loading of RNA.

FIG. 4B top: Northern analysis of corresponding cell lines for detection of expression of crmA transcript. FIG. 4B bottom: Northern analysis to detect β-actin transcript to assess loading RNA.

FIGS. 5A through 5C show the nucleic acid sequence and corresponding amino acid sequence of the cowpox crmA gene and gene product. (Seq. ID. Nos. 3 and 4, respectively.)

DETAILED DESCRIPTION OF THE INVENTION

Figure 1A:
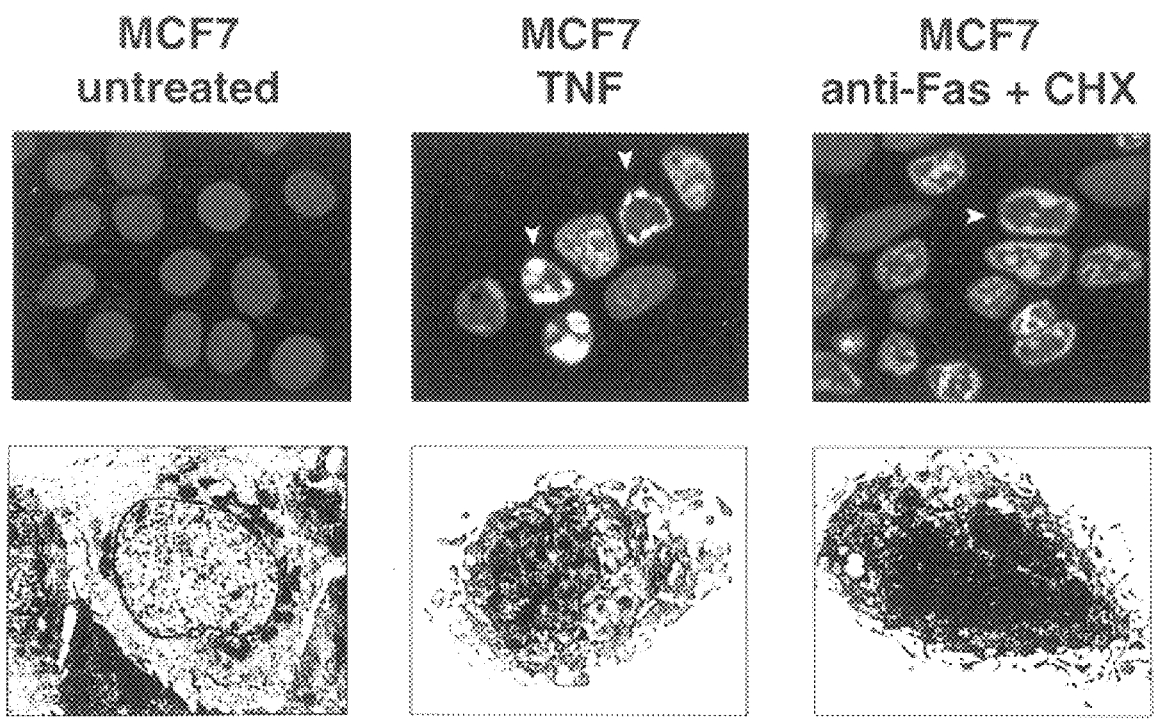
FIG. 1A shows TNF and anti-Fas+CHX induce apoptosis in MCF7 cells. MCF7 cells were treated with TNF or anti-Fas+CHX as described in the experimental section below. Upper row: Nuclei of untreated, TNF treated, or anti-Fas+CHX treated MCF7 cells stained with propidium iodide and visualized by laser-scanning confocal microscopy. Arrows indicate examples of apoptotic nuclei. Lower row: Transmission electron microscopy of untreated, TNF treated or anti-Fas+CHX treated MCF7 cells.

As is known to those of skill in the art, apoptosis is an active process of gene-directed cellular self-destruction. This invention provides compositions and methods for preventing or inhibiting apoptosis in a suitable cell or a population of suitable cells by introducing into the cell or cells an effective amount of a nucleic acid molecule coding for a gene product having crmA biological activity. The method also may be practiced using the gene product itself. It is important to note that the method of this invention inhibits apoptosis even in the presence of apoptotic-inducing agents, such as receptor ligands, e.g., anti-TCR, tumor necrosis factor (TNF), HIV, SIV or anti-Fas antibody. Accordingly, this method provides an improvement over prior art methods wherein apoptosis can be inhibited by interfering with the induction pathway at the level of ligand induction, such as by providing antibodies or anti-ligand antibodies to interfere with the binding of the ligand to its cell surface receptor. However, this invention can be combined with the use of such prior art methods to inhibit apoptosis.

The terms "preventing" or "inhibiting" are intended to mean a reduction in cell death or a prolongation in the survival time of the cell. They also are intended to mean a diminution in the appearance or a delay in the appearance of morphological and/or biochemical changes normally associated with apoptosis. Thus, this invention provides compositions and methods to increase survival time and/or survival rate of a cell or population of cells which, absent the use of the method, would normally be expected to die. Accordingly, it also provides compositions and methods to prevent or treat diseases or pathological conditions associated with unwanted cell death in a subject.

Suitable cells or "target cells" for the practice of this method include, but are not limited to, cells that are induced to PCD by an endogenous agent such as HIV, anti-TCR antibody, TNF and anti-Fas antibody. In one embodiment, these cells constitutively and inducibly express receptors for either or both of the cytokine tumor necrosis factor (TNF) or the cell death transducing receptor Fas or TCR and which have been activated by their respective ligand. Recently, three separate groups have reported that Fas-induced apoptosis is involved in T cell death. Specifically, one group has shown that the Fas receptor, which can transduce a potent apoptotic signal when ligated, is rapidly expressed following activation on T cell hybridomas. It was suggested that the Fas receptor-ligand interaction induces cell death in a cell-autonomous manner. See Dhein et al. (1995) *Nature* 373:438–441; Brunner et al. (1995) *Nature* 373:441–444; and Ju et al. (1995) *Nature* 373:444–448.

For the purpose of illustration only, examples of suitable cells are T lymphocytes (T cells) (e.g., $TCR^+$, $CD4^+$ and $CD8^+$ T cells) leukocytes and mixed leukocyte cultures (MLC), B lymphoma cells (e.g., A202J (ATCC)), bone marrow cells, endothelial cells, breast carcinoma cells, fibroblast cells, epithelial tumor cells (see Spriggs, D. R. et al. (1988) *J. Clin. Inves.* 81:455–460) and monocytes. Fas and TNF receptor expression also has been identified on numerous tissues, see for example Watanabe-Fukunaga et al. (1992) *J. Immun.* 148:1274–1279 and Owen-Schaub, L. B. et al. (1994) *Cancer Res.* 54:1580–1586; Dhein et al. (1995) *Nature* 373:438–441; Brunner et al. (1995) *Nature* 373:441–444; and Ju et al. (1995) *Nature* 373:444–448. Assays for identifying additional "suitable" cells sensitive to induction or activation, e.g., TCR-, TNF- or Fas-related apoptosis, are well known to those of skill in the art. (See for example, Opipari, et al. *J. Biol. Chem.* (1992) 267:12424–12427; Yonehara et al. *J. Exp. Med.* (1989) 169:1747–1756; Dhein et al. (1995) supra; Brunner et al. (1995) supra and Ju et al. (1995) supra) However, this method is particularly suitable for use with $TCR^+$, $CD8^+$ or $CD4^+$ T cells or tissues that harbor the simian immunodeficiency virus (SIV) or alternatively, the human immunodeficiency virus (HIV). The cells can be mammalian cells or animal cells, such as guinea pig cells, rabbit cells, simian cells, mouse cells, rat cells, or human cells. They can be continuously cultured or isolated from an animal or human. In a separate embodiment of this invention, neurological cells are specifically excluded.

This invention is based on Applicants' finding that the cowpox virus crmA gene product is an exceptionally potent inhibitor of apoptosis induced by binding of a cell surface receptor to its ligand, e.g., TCR ligand, HIV, Fas or TNF. In one embodiment which utilized TNF- and Fas- pathways; it is capable of blocking the cell death program even at pharmacological doses of the death stimulus. crmA is a cowpox virus gene which encodes a protease inhibitor of the serpin family. The nucleic acid and corresponding amino acid sequences of crmA have been reported (Pickup et al., *Proc. Natl. Acad. Sci.* (1986) 83:7698–7702) and are shown in FIG. 5.

The only reported target for the crmA protein is the cysteine protease interleukin-1β converting enzyme (ICE). However, Applicants have found that crmA is an exceptionally potent inhibitor of apoptosis. Therefore, an important new function for crmA is the prevention or inhibition of ligand-induced or cytokine-induced apoptosis. Further, the data suggest that a protease, either ICE or a related crmA-inhibitable protein, is a component of the Fas- and TNF-induced cell death pathways. Thus, this invention provides: compositions and methods for preventing or inhibiting ligand-induced or cytokine-induced apoptosis; an assay for determining drugs or agents which facilitate or prevent or inhibit apoptosis; an assay for drugs to treat or ameliorate the symptoms associated with a disease or pathological conditions that occur as a result of apoptosis (such as AIDS); an assay for detecting the protease involved in the Fas- and TNF- induced cell death pathways, as well the proteases discovered using this method.

The crmA gene or nucleic acid can be isolated from natural or native sources as described in Pickup et al. (1986) supra. The term "native" refers to the form of a nucleic acid, protein, polypeptide, antibody or a fragment thereof that is isolated from nature or which is without an intentional amino acid substitution. As used herein, "nucleic acid" and "gene" are synonymous and shall mean single and double stranded genomic DNA, cDNA, mRNA and cRNA. "Isolated" when used to describe the state of the nucleic acids or proteins, denotes the nucleic acids or proteins free of at least a portion of the molecules associated with or occurring with nucleic acids in their native environment.

Reference is made to standard textbooks of molecular biology that contain definitions and methods and means for carrying out basic techniques, encompassed by the present invention. See, for example, Maniatis et al., *Molecular Cloning: A Laboratory Manual,* Cold Spring Harbor Laboratory, New York (1982) and Sambrook et al., *Molecular Cloning: A Laboratory Manual,* Cold Spring Harbor Laboratory, New York (1989) and the various references cited therein. This reference and the cited publications are expressly incorporated by reference into this specification.

The DNA sequence provided in FIG. 5 can be duplicated using a DNA sequencer and methods well known to those of skill in the art. For example, the sequence can be chemically replicated using PCR (Perkin-Elmer) which in combination with the synthesis of oligonucleotides, allows easy reproduction of DNA sequences. A DNA segment of up to approximately 6000 base pairs in length can be amplified exponentially starting from as little as a single gene copy by means of PCR. In this technique, a denatured DNA sample is incubated with two oligonucleotide primers that direct the DNA polymerase-dependent synthesis of new complementary strands. Multiple cycles of synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202.

The nucleic acid can be duplicated using a host-vector system and traditional cloning techniques with appropriate replication vectors. A "host-vector system" refers to host cells which have been transfected with appropriate vectors using recombinant DNA techniques. The vectors and methods disclosed herein are suitable for use in host cells over a wide range of eucaryotic organisms. This invention also encompasses the cells transformed with the novel replication and expression vectors described herein.

Indeed, the crmA gene can be duplicated in many replication vectors such as the vaccinia virus as described in Pickup et al. (1986) supra, and isolated using methods described in Sambrook et al. (1989) supra.

The crmA gene made and isolated using the above methods can be directly inserted into an expression vector, such pcDNA3 (Invitrogen) and inserted into a suitable animal or mammalian cell such as a guinea pig cell, a rabbit cell, a simian cell, a mouse, a rat or a human cell.

In the practice of one embodiment of this invention, the crmA nucleic acid molecule is introduced into the cell and expressed and cell death is aborted. A variety of different gene transfer approaches are available to deliver the crmA gene into a target cell, cells or tissues. Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens, e.g., TCR, CD3 or CD4. Liposomes that also comprise a targeting antibody or fragment thereof can be used in the methods of this invention. This invention also provides the targeting complexes for use in the methods disclosed herein.

The crmA nucleic acid also can be incorporated into a "heterologous DNA" or "expression vector" for the practice of this invention. The term "heterologous DNA" is intended to encompass a DNA polymer such as viral vector DNA, plasmid vector DNA or cosmid vector DNA. Prior to insertion into the vector, it is in the form of a separate fragment, or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. As used herein, "recombinant" is intended to mean that a particular DNA sequence is the product of various combination of cloning, restriction, and ligation steps resulting in a construct having a sequence distinguishable from homologous sequences found in natural systems. Recombinant sequences can be assembled from cloned fragments and short oligonucleotides linkers, or from a series of oligonucleotides.

As noted above, one means to introduce the nucleic acid into the cell of interest is by the use of a recombinant expression vector. "Recombinant expression vector" includes vectors which are capable of expressing DNA sequences contained therein, where such sequences are operatively linked to other sequences capable of effecting their expression. It is implied, although not always explicitly stated, that these expression vectors must be replicable in the host organisms either as episomes or as an integral part of the chromosomal DNA. In sum, "expression vector" is given a functional definition, and any DNA sequence which is capable of effecting expression of a specified DNA sequence disposed therein is included in this term as it is applied to the specified sequence. Suitable expression vectors include viral vectors, including adenoviruses, adeno-associated viruses, retroviruses, cosmids and others. Adenoviral vectors are a particularly effective means for introducing genes into tissues in vivo because of their high level of expression and efficient transformation of cells both in vitro and in vivo.

Replication-incompetent retroviral vectors also can be used with this invention. As used herein, the term "retroviral" includes, but is not limited to, a vector or delivery vehicle having the ability to selectively target and introduce the coding sequence into dividing cells, such as the mouse molony-leukemia virus. As used herein, the terms "replication-incompetent" is defined as the inability to produce viral proteins, precluding spread of the vector in the infected host cell. As should be understood by those of skill in the art, crmA nucleic acid will be ribonucleic acid (RNA) for introduction with a retroviral vector.

Another example of a replication-incompetent retroviral vector is LNL6 (Miller, A. D. et al., *BioTechnicues* 7:980–990 (1989)). The methodology of using replication-incompetent retroviruses for retroviral-mediated gene transfer of gene markers is well established (Correll, P. H. et al., (1989) *PNAS USA* 86:8912; Bordignon, C. et al., *PNAS USA* (1989) 86:6748–52; Culver, K. et al., (1991) *PNAS USA* 88:3155; Rill, D. R. et al., (1990) *Blood* 79(10):2694–700). Clinical investigations have shown that there are few or no adverse effects associated with these viral vectors (Anderson, (1992) *Science* 256:808–13).

In one embodiment of this invention, the expression vector is to be specifically targeted to T cells. For these methods, it intended that the crmA DNA be operatively linked to a promoter that is highly active in T cells. Such promoters include, but are not limited to: IFN-τ; IL-2; IL-3; IL-4; IL-5; IL-9; IL-10; TFN-β; GM-CSF; CD4, CD8 and the IL-2 promoter.

Although the method is preferably practiced with the crmA gene, it should be apparent to those of skill in the art that the polypeptide product of the crmA gene and its biological equivalents are useful in the methods of this invention. The crmA gene product is a 38 kDa protein and is known to be a specific inhibitor of IL-1β. It can be purified from natural sources as described in Ray, C. A. (1992) Cell 69:597–604 or produced recombinantly using the expression vectors described above in a host-vector system such as described in Pickup et al. (1986) supra, Ray et al. (1992) supra and Moss, B. ed. (1990) Virology, pp:2079–2112, Raven Press, N.Y. The protein is used in substantially pure form. By "substantially pure," it is meant that the protein is substantially free of other biochemical moieties with which it is normally associated in nature. The proteins also can be produced using the sequence provided in FIG. 5 and methods well known to those of skill in the art.

Accordingly, this invention also provides a crmA polypeptide, protein, a biological equivalent thereof and fusion proteins containing these, for use in the methods described herein. The polypeptides or proteins can be conjugated to targeting antibodies, such as anti-CD3 or anti-CD4 for targeted delivery to T cells.

A "biological equivalent" is intended to mean any fragment of the nucleic acid or protein, a mimetic (protein and non-protein mimetic) also having the ability to inhibit apoptosis using the assay system described and exemplified herein. For example, purified crmA polypeptide can be contacted with a suitable cell as described above and under such conditions that apoptosis is inhibited. It is understood that limited modifications can be made to the primary sequence of the crmA sequence as shown in FIG. 5 and used in this invention without destroying its biological function, and that only a portion of the entire primary structure may be required in order to effect biological activity. Examples of such biological equivalent fragments include, but are not limited to the 5.2 kb EcoRI fragment or the 2.7 kb BglII fragment and the polypeptides encoded by these nucleic acid molecules as described in Pickup et al. (1986) supra. It is further understood that minor modifications of the primary amino acid sequence may result in proteins which have substantially equivalent or enhanced function as compared to the molecule within the vector. These modifications may be deliberate, as through site-directed mutagenesis, or may be accidental such as through mutation in hosts. All of these modifications are included as long as the ability to inhibit apoptosis is retained.

This method can be practiced in vitro, ex vivo or in vivo. When the method is practiced in vitro, the expression vector, protein or polypeptide can be added to the cells in culture or added to a pharmaceutically acceptable carrier as defined below. In addition, the expression vector or crmA DNA can be inserted into the target cell using well known techniques such as transfection, electroporation or microinjection.

More specifically, the in vitro method comprises providing cell cultures or tissue cultures having either a cell surface receptor that mediates apoptosis such as a TCR, the TNF receptor or the Fas receptor. The cells are cultured under conditions (temperature, growth or culture medium and gas ($CO_2$)) and for an appropriate amount of time to attain exponential proliferation without density dependent constraints. The cells are then exposed to preliminary conditions necessary for apoptosis, for example an effective amount of an inducing agent, e.g., a TCR ligand, HIV, SIV, TNF, or a Fas ligand such as an anti-Fas antibody is added to the culture. Anti-Fas antibodies and mitogens (ConA) are well known to those of skill in the art. (Itoh, N. et al. (1991) Cell 66:233–243 and Yonehara et al. (1989) J. Exp. Med. (1989) 169:1747–1756). These cells are now "induced" to apoptosis. The cells are again cultured under suitable temperature and time conditions. In one embodiment, HIV or SIV is added to the culture. In other embodiments, a drug or agent to be tested is added in varying concentrations at a time that is simultaneous with, prior to, or after the inducing agent.

The crmA nucleic acid or protein is then added to the culture in an effective amount and the cells are cultured under suitable temperature and time conditions to inhibit apoptosis. The crmA nucleic acid or protein can be added prior to, simultaneously with, or after, the inducing agent. The cells are assayed for apoptotic activity using methods well known to those of skill in the art and described herein. It is apparent to those of skill in the art that two separate culture of cells must be treated and maintained as the test population. One is maintained without receiving an inducing agent to determine background release and the second without receiving the agent to be tested. The second population of cells acts as a control.

The use of the compositions and methods in vitro provides a powerful bioassay for screening for drugs which are agonists or antagonists of crmA function in these cells. Thus, one can screen for drugs having similar or enhanced ability to prevent or inhibit apoptosis. It also is useful to assay for drugs having the ability to inhibit HIV infection and replication, since the $CD4^+$ cell will not die as a result of the concurrent viral infection. One of skill in the art can determine when the method has been successfully performed by noting the absence of apoptotic morphological changes or more simply, by the absence of cell death. The in vitro method further provides an assay to determine if the method of this invention is useful to treat a subject's pathological condition or disease that has been linked to apoptotic cell death in the individual.

For example, a T cell hybridoma cell line such as Jurkat can be stably transfected with the crmA expression construct or vector alone and clonal cell lines derived. Transfection of Jurkat cell by electroporation can be performed as described in Laherty et al. J. Biol. Chem. (1993) 263:5032–5039. crmA-expressing and vector-transfected control cells are $^{51}Cr$-labeled and plated ($5 \times 10^5$/ml) on untreated or anti-CD3 (available from the cell line 145-2C11 (ATCC)) treated tissue culture plastic plates. Cells cultured on uncoated cells are used to determine background release. The percentage cell death will be determined at various times after culture by the formula: c.p.m. released from the experimental group minus c.p.m. of background release divided by c.p.m. released by 0.5% Triton X-100 (complete lysis)—c.p.m. of background release.

A substantial decrease in percent cell death induced by plating cells on immobilized anti-CD3 monoclonal antibody is an indication that crmA inhibits T cell receptor-induced death. Using the method described above, various agents can be tested for their ability to inhibit or prevent apoptosis.

In a separate embodiment, the T cell line designated CEM (ATCC) is obtained and used because it has been shown to undergo PCD upon infection with HIV. CEM cells are transfected by electroporation with the crmA expression construct and vector alone as control. Clonal lines are derived and infected at various multiplicity of infection ratios with HIV. Cytopathic effect is assayed by microscopic observation and apoptosis quantitated following propidium iodine staining. Using the method described above, various agents can be tested for their ability to inhibit or prevent apoptosis.

When the method is practiced in vivo in a human patient, it is unnecessary to provide the inducing agent since it is provided by the patient's immune system. However, when practiced in an experimental animal model, it can be necessary to provide an effective amount of the inducing agent in a pharmaceutically acceptable carrier prior to administration of the crmA product, to induce apoptosis. When the method is practiced in vivo, the carrying vector, crmA polypeptide, polypeptide equivalent, or crmA expression vector can be added to a pharmaceutically acceptable carrier and systemically administered to the subject, such as a human patient or an animal such as a mouse, a guinea pig, a simian, a rabbit or a rat. Alternatively, it can be directly infused into the cell by microinjection. A fusion protein also can be constructed comprising the protease-inhibitory region of the crmA, diphtheria toxin and a T-cell specific ligand for targeting to a T cell. Such T cell specific ligands include, but are not limited to anti-CD3, anti-CD4, anti-CD28 and anti-IL-1 antibody protein.

Acceptable "pharmaceutical carriers" are well known to those of skill in the art and can include, but not be limited to any of the standard pharmaceutical carriers, such as phosphate buffered saline, water and emulsions, such as oil/water emulsions and various types of wetting agents.

When practiced in vivo, the compositions and methods are particularly useful for maintaining T cell viability and function in a subject or an individual suffering from or predisposed to suffer from abnormal lymphocyte death. When the animal is an experimental animal such as a simian (using SIV), this method provides a powerful assay to screen for new drugs that may be used alone or in combination with this invention to ameliorate or reduce the symptoms and opportunistic infections associated with HIV infection or AIDS.

This invention also is particularly useful to ward off lymphocyte death or immunosuppression in AIDS patients. By preventing or inhibiting apoptosis, not only is cell death prevented but functionality, e.g., immuno-proliferative capacity, is restored to the cell and a responsive immune system is retained or regained. Accordingly, the compositions and methods of this invention are suitably combined with compositions and methods which prevent or inhibit HIV infectivity and replication.

The method can also be practiced ex vivo using a modification of the method described in Lum et al. (1993) *Bone Marrow Transplantation* 12:565–571. Generally, a sample of cells such as bone marrow cells or MLC can be removed from a subject or animal using methods well known to those of skill in the art. An effective amount of crmA nucleic acid is added to the cells and the cells are cultured under conditions that favor internalization of the nucleic acid by the cells. The transformed cells are then returned or reintroduced to the same subject or animal (autologous) or one of the same species (allogeneic) in an effective amount and in combination with appropriate pharmaceutical compositions and carriers.

As used herein, the term "administering" for in vivo and ex vivo purposes means providing the subject with an effective amount of the nucleic acid molecule or polypeptide effective to prevent or inhibit apoptosis of the target cell. Methods of administering pharmaceutical compositions are well known to those of skill in the art and include, but are not limited to, microinjection, intravenous or parenteral administration. The compositions are intended for topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the vector used for therapy, the polypeptide or protein used for therapy, the purpose of the therapy, the target cell being treated, and the subject being treated. Single or multiple administrations can be carried out with the dose level and pattern being selected by the treating physician. For example, the compositions can be administered prior to a subject already suffering from a disease or condition that is linked to apoptosis. In this situation, an effective "therapeutic amount" of the composition is administered to prevent or at least partially arrest apoptosis and the accompanying pathology such as immunosuppression in HIV infected individuals.

However, the compositions can be administered to subjects or individuals susceptible to or at risk of developing apoptosis-related disease to prevent pathological cell death. In one embodiment, the composition can be administered to a subject susceptible to HIV-related lymphocyte disfunction to maintain lymphocyte cell function and viability. In these methods a "prophylactically effective amount" of the composition is administered to maintain cellular viability and function at a level near to the pre-infection level.

It should be understood that by preventing or inhibiting unwanted cell death in a subject or individual, the compositions and methods of this invention also provide methods for treating, preventing or ameliorating the symptoms associated with a disease characterized by apoptosis of cells. Such diseases include but are not limited to AIDS, acute and chronic inflammatory disease, leukemia, myocardial infarction, stroke, traumatic brain injury, neural and muscular degenerative diseases, aging, tumor induced-cachexia and hair loss.

This invention also provides vector and protein compositions useful for the preparation of medicaments which can be used for preventing or inhibiting apoptosis, maintaining cellular function and viability in a suitable cell or for the treatment of a disease characterized by the unwanted death of target cells.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

Experiment I

Analysis of Apoptosis—Apoptosis was assessed by the use of fluorescent DNA-staining dyes to reveal nuclear morphology and by transmission electron microscopy. For propidium iodide staining, MCF7 cells were grown on 22 $mm^2$ No. 1 glass coverslips (Corning) placed in 35 mm wells of a 6-well culture dish (Costar). Following treatment with TNF, anti-Fas cycloheximide (CHX), or no treatment, medium was removed and the wells were rinsed twice with phosphate buffered saline (PBS), fixed in 100% methanol at −20° C. for 10 minutes, washed three times with PBS, and stained at room temperature for 10 minutes in a 100 $\mu$g/ml solution or propidium iodide (Sigma) made in PBS. The coverslips were then washed three times with PBS, blotted dry and mounted onto glass slides using Vectashield mounting medium for fluorescence (Vector Laboratories). BJAB cells were stained using acridine orange (SIGMA) by preparing a wet mount of 30 $\mu$l of a cell suspension at a density of approximately $3\times10^5$ cell/ml mixed with 5 $\mu$l of a 100 $\mu$g/ml acridine orange solution made in PBS. Both propidium iodide-stained MCF7 and acridine orange-stained BJAB nuclei were visualized by fluorescence microscopy using a FITC range barrier filter cube. Laser-scanning confocal microscopy was performed using the Bio-Rad MRC 600 confocal microscope and digitized images obtained were artificially colorized.

For electron microscopy, cells were fixed and processed as per standard electron microscopy procedures.

Experiment II

Quantitative Apoptosis Assays—MCF7 cells or derived transfectants were plated at a concentration of $2.5 \times 10^5$ cells/well onto glass coverslips. Two days later, after the cells had adhered and spread, TNF or anti-Fas+CHK were added. TNF was added at a final concentration of 20 ng/ml, anti-Fas at 25 ng/ml, and CHX (Sigma) at 10 $\mu$g/ml. After 22 hours for the TNF treated samples or after 18 hours for the anti-Fas+CHX treated samples, cells were fixed, stained with propidium iodide and mounted as described above. Apoptotic and non-apoptotic cells were quantitated based on nuclear morphology using fluorescence microscopy and the percentage of non-apoptotic cells was calculated. A minimum of 100 cells was counted for each sample, and each experiment was done at least in duplicate. Since a small fraction of cells in any normally growing cell culture is undergoing apoptosis, spontaneous apoptosis in untreated or CHX alone treated samples was also quantitated. The percentage of non-apoptotic cells in the TNF or anti-Fas+CHX treated samples was then normalized by correcting for the frequency of spontaneous apoptosis in the untreated or CHX alone samples, respectively.

BJAB cells were grown at $3 \times 10^5$ cells/ml and treated with anti-Fas antibody at a concentration of 250 ng/ml (unless indicated otherwise) for 18 hours after which an aliquot was stained with acridine orange as described above. Apoptotic cells and non-apoptotic cells were quantitated and normalized to untreated samples. Assays were done at least in duplicate.

Secondary assays of cell death used were the MTT conversion assay (as described in Opipari, A. W. et al. *J. Biol. Chem.* (1992) 267:12424–12427) and crystal violet staining and were done as described in Tartaglia, L. A. et al. (1993) *Cell* 74:845–853.

Plasmids, Transfections and Selection of Stably Transfected Lines—The crmA gene as shown FIG. 5 was cloned into the pcDNA3 (Invitrogen) mammalian expression vector. The crmA gene was obtained from Dr. David Pickup (Duke University) and used as a template in a PCR reaction using custom oligonucleotide primers with built-in restriction enzyme sites to amplify the entire coding sequence. The sequence of the primers are:
crmA/5'/R1
5' CAC CGG AAT TCC ACC ATG GAT ATC TTC AGG GAA ATC G
(Seq. ID. No. 1)
crmA/3'/XbaI
5' GCT CTA GAC TCG AGT TAA TTA GTT GTT GGA GAG CAA TAT C
(Seq. ID. No. 2)
This PCR fragment was digested with EcoR1 and XbaI restriction enzymes and subcloned into the pcDNA3 vector which had been similarly digested. Following transformation into competent XL-1Blue host *E. coli* cells (Stratagene), individual colonies were grown up, plasmid extracted and the presence of the crmA gene confirmed by both restriction mapping and DNA sequence analysis.

The resulting expression construct or pcDNA3 itself (as the control) was introduced into both MCF7 and BJAB cells by electroporation. MCF7 cells were electroporated at 330 V, 960 $\mu$F in 0.4 cm cuvettes (BioRad), plated onto 100 mm dishes at varying dilutions and selected with G418 sulfate (Gibco-BRL) at a concentration of 500 $\mu$g/ml. After selection for three weeks, pooled populations from each transfection were prepared by trypsinizing dishes containing several hundred colonies. Additionally, clonal cells lines were derived by picking individual colonies from selected dishes. BJAB cells were electroporated at 220 V, 960 $\mu$F in 0.4 cm cuvettes (Bio-Rad) and selected in 3 mg/ml G418 sulfate. One day following transfection, a portion of the cell population was diluted at a concentration of 2500 cells/well in 96-well dishes from which clonal lines were obtained after G418 selection. The remainder of the cells were retained as the pooled population.

Experiment III

Cell Lines, TNF and Anti-Fas Antibody—The MCF7 cell line was a TNF-sensitive subclone obtained from Dr. David R. Spriggs (University of Wisconsin). MCF7 is a breast carcinoma epithelial cell line which expresses TNF receptor and is sensitive to TNF killing. The BJAB cell line was a gift of Dr. Fred Wang (Harvard). Recombinant TNF (specific activity $6.27 \times 10^7$ U/mg) was obtained from Genentech (South San Francisco, Calif.). Anti-Fas monoclonal antibody (clone CH-11, IgM) was obtained from Pan Vera (Madison, Wis.).

RNA Isolation and Northern Analysis—RNA isolation and northern analysis were carried out as described in Dixit, V. M. et al. (1990). *J. Biol Chem.* 265:2973–2978. PCR (Perkin-Elmer) was used to generate a probe spanning the coding region of the crmA gene as described above. $\beta$-actin cDNA probe was purchased from Clontech (Palo Alto, Calif.) and the hybridization signal was visualized as a digitized image on a Molecular Dynamics Phosphorimager.

Experiment IV

Induction of Apoptosis by TNF and anti-Fas—A subclone of the MCF7 breast carcinoma epithelial cell line which expressed TNF receptor and was sensitive to TNF killing was chosen for these studies. This cell line is characterized in Spriggs, D. R. et al. (1988) *J. Clinc. Invest.*, 81:455–460. Further analysis revealed that Fas was also expressed on these cells and that crosslinking with an anti-Fas monoclonal antibody in the concomitant presence of the protein synthesis inhibitor cycloheximide induced cell death.

Cycloheximide aline for the duration of the assay did not induce cell death beyond the negligible frequency of spontaneous apoptosis which is observed in any untreated cell culture. Anti-Fas alone was not cytotoxic, but this is not surprising, since induction of cell death in non-lymphoid cells by Fas activation has been reported to require the concomitant presence of either transcriptional or translational inhibitors. See Itoh, N. et al. (1991) *Cell* 66:233–243.

A B-cell lymphoma cell line (BJAB) also was examined. It expresses a high level of Fas and was killed by the addition of anti-Fas antibody in the absence of a protein synthesis inhibitor.

Figure 1B:
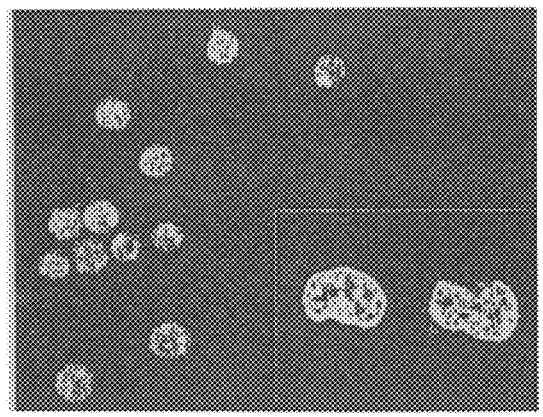
FIG. 1B shows that anti-Fas antibody induces apoptosis in BJAB cells. BJAB cells were treated with anti-Fas antibody as described below. The Figure shows fluorescence microscopy of untreated or anti-Fas treated BJAB cells stained with acridine orange. Arrows indicate examples of apoptotic nuclei. Inset: Laser scanning confocal microscopy of untreated or anti-Fas treated BJAB cells stained with acridine orange.
Figure 1B:
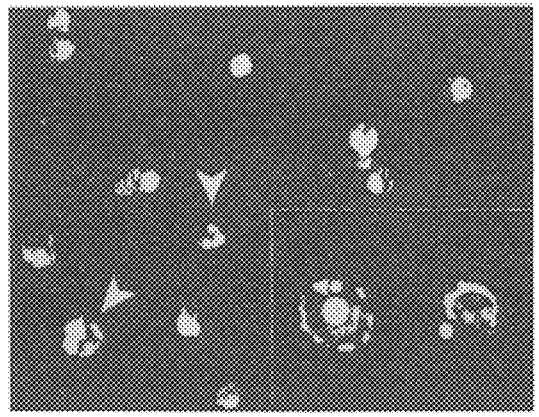
Figure 2:
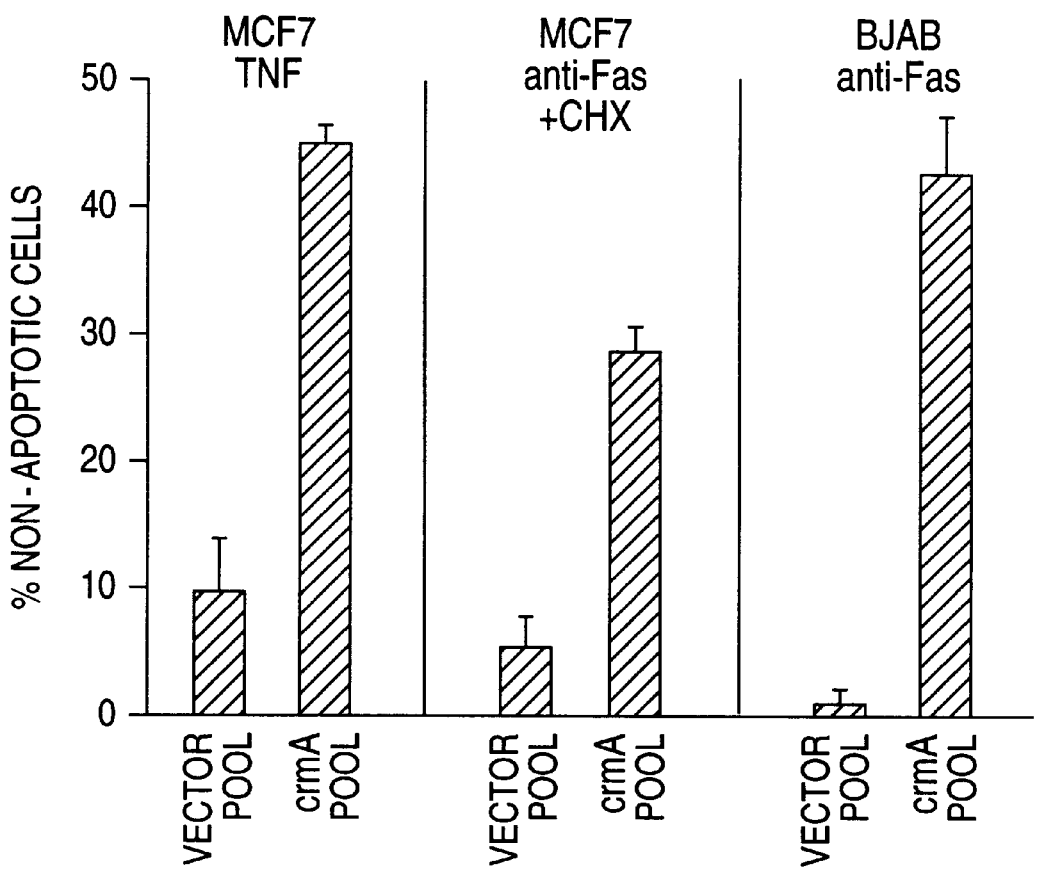
FIG. 2 shows inhibition of apoptosis by crmA in pooled populations of transfectants. Pooled populations of the vector or crmA transfected cells indicated were analyzed for sensitivity to TNF- or Fas-mediated apoptosis.

Cell death can occur by two biochemically and morphologically distinct processes: apoptosis and necrosis. In these studies, cell death was first confirmed to be the result of TNF or anti-Fas induced apoptosis, not necrosis. Although various markers of apoptosis have been reported, the phenomenon is preferably defined at the morphological level and is characterized by chromatin condensation and margination along the inner nuclear membrane, cytoplasmic condensation and membrane blebbing without disintegration of the cellular membrane. See Duvall E. et al. (1986) *Immunol. Today* 7:115–119. Necrosis, conversely, is defined by cytoplasmic swelling and lysis of the cell membrane and, importantly, does not exhibit the chromatin margination characteristic of apoptosis. DNA laddering, representative of cleavage at internucleosomal intervals, is seen in some but not all forms of apoptosis, further emphasizing the importance of morphological criteria in defining apoptosis. See Barres, B. A. et al. (1992) *Cell* 70:31–46. Nuclear morphology of cells dying in response to TNF or anti-Fas antibody was examined following staining with the DNA-binding dyes propidian iodine (MCF7 cells) and acridine orange (BJAB cells). Fluorescence microscopy laser scanning confocal microscopy demonstrated marked changes in nuclear morphology in the MCF7 cells in response to either TNF or anti-Fas-CHX and in the BJAB cells in response to anti-Fas. Chromatin condensation was clearly visible by immunofluorescence microscopy in both cell lines and formed the basis for the later assays of apoptosis in transfected cell lines (FIG. 1B for BJAB). Confocal microscopy confirmed margination along the inner nuclear membrane (FIGS. 1A and 1B inset). These morphological criteria of apoptotic cell death were further confirmed by transmission electron microscopy. The MCF7 cells clearly demonstrated chromatin condensation and margination along the inner nuclear membrane, cytoplasmic condensation and increased membrane blebbing in response to either TNF or anti-Fas+CHX (FIG. 1A). BJAB cells treated with anti-Fas antibody demonstrated chromatin margination and cellular shrinkage typical of apoptosis in lymphoid cells. Thus, both TNF and Fas induced genuine apoptotic cell death in these cell lines.

Experiment V crmA Blocks TNF- and anti-Fas-Induced Apoptosis—To determine whether crmA can function to inhibit cytokine-induced apoptosis, MCF7 and EJAB cell lines were transfected with either the expression vector pcDNA3 by itself or as a crmA expression construct. Expression of the crmA gene was confirmed by northern analysis. Stable transfectants were generated by neomycin selection, and pooled populations of neomycin-resistant cells were assayed for crmA expression. These pooled populations were analyzed for their sensitivity to TNF- and anti-Fas-induced apoptosis by direct quantitation of apoptotic cells based on nuclear morphology following staining with DNA-binding dyes and visualization by fluorescence microscopy. Dramatic resistance was seen with either TNF or Fas in both cell lines. This was remarkable, given that in the pooled population of neomycin-resistant cells transfected with crmA, a significant fraction of cells were likely not expressing crmA due to, among other reasons, nonproductive integration of the expression construct into genomic DNA.

Figure 3A:
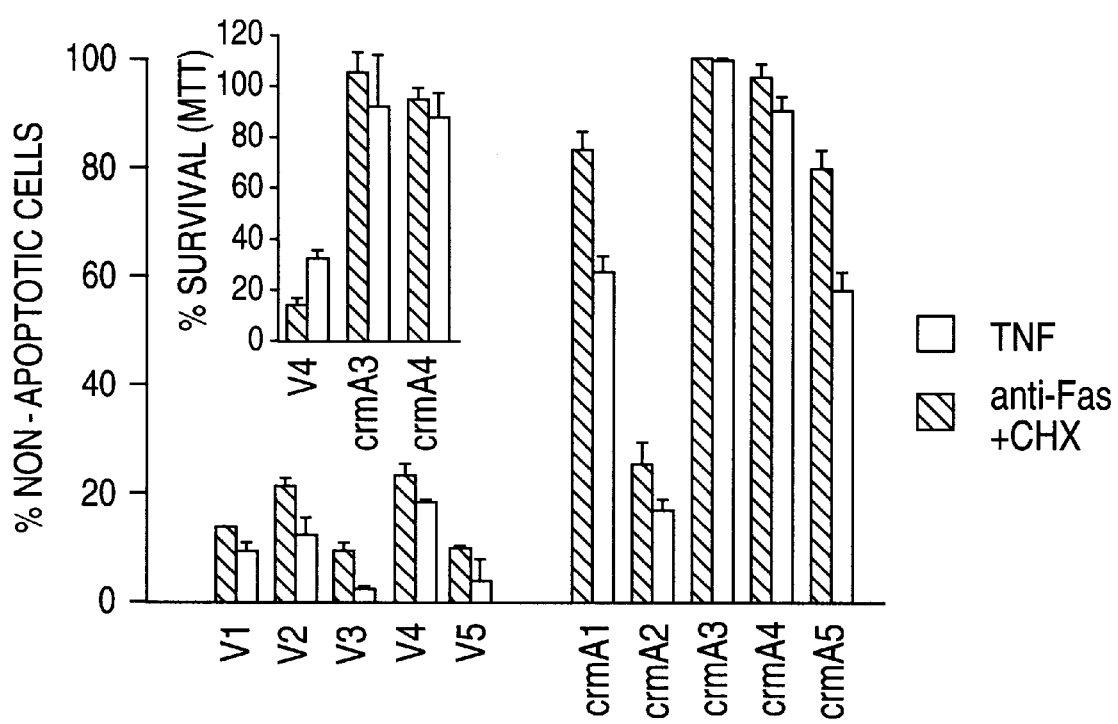
FIG. 3A shows inhibition of TNF and anti-Fas+CHX induced apoptosis of MCF7 cells by crmA. Top: Sensitivity of MCF7 vector transfected clones (V1–V5) or crmA transfected clones (crmA1 to crmA5) to TNF and anti-Fas+CHX induced cell death assessed by propidium iodine apoptosis assay. Insert: Sensitivity of selected clones to TNF and anti-Fas+CHX induced cell death by MTT conversion assay.
Figure 3B:
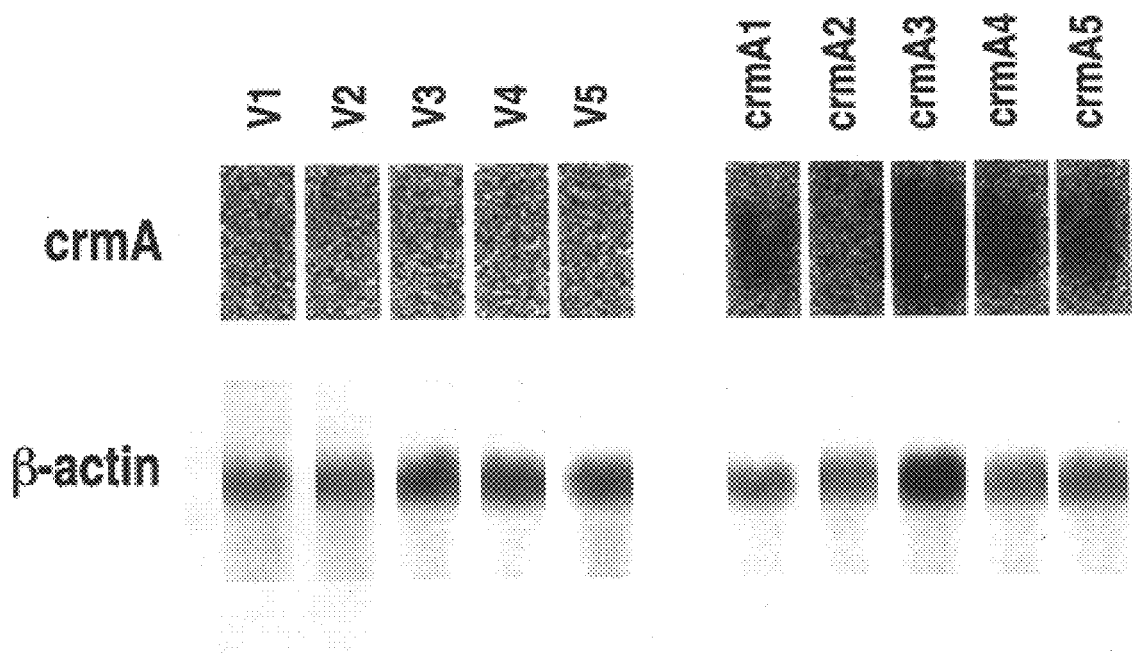
Figure 3C:
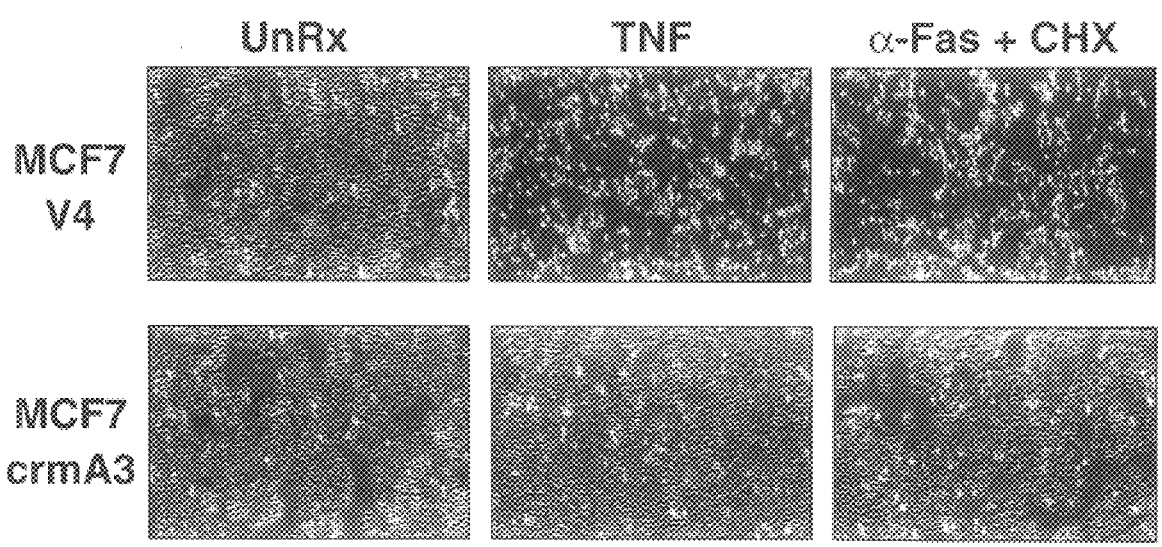
FIG. 3C shows crmA-mediated inhibition of apoptosis induced by increasing doses of anti-Fas antibody.
Figure 3D:
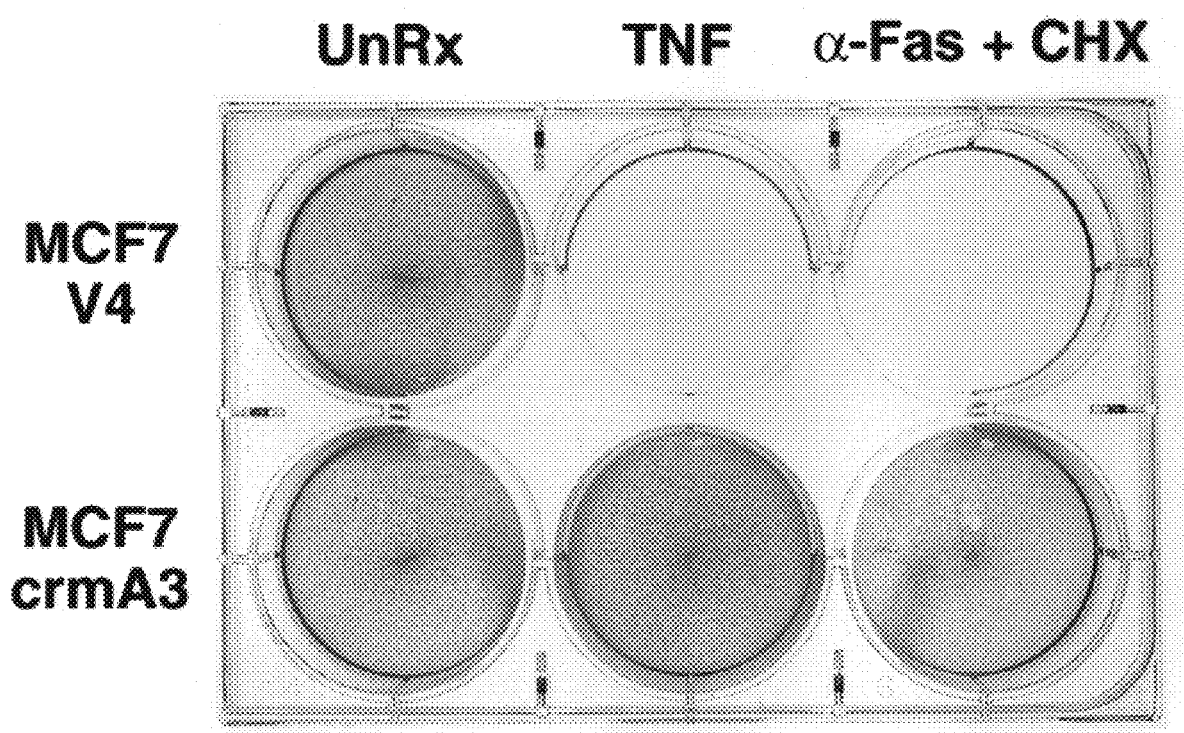
FIG. 3D shows crmA inhibits apoptosis induced by increasing doses of anti-Fas antibody. The acridine orange apoptosis assay was used to analyze the sensitivity of vector transfected (BJAB V1) or crmA-transfected (BJAB crmA2, BJAB crmA3) clones to apoptosis induced by the indicated doses of anti-Fas antibody.
Figure 4A:
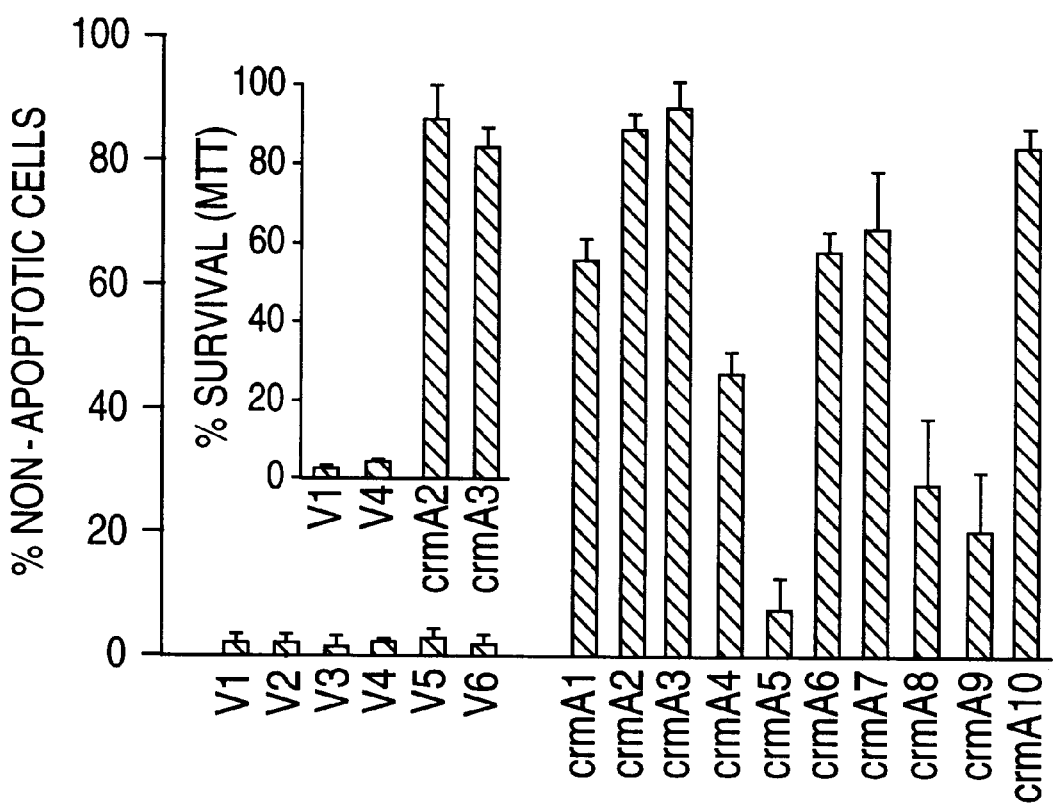
FIG. 4A shows inhibition of anti-Fas induced apoptosis in BJAB cells by crmA. Top: Analysis of sensitivity of BJAB vector transfected clones (V1–V6) or crmA transfected clones (crmA1–crmA10) to anti-Fas induced apoptosis. Cell death was assessed by acridine orange apoptosis assay. Insert: Sensitivity of selected clones to anti-Fas induced cell death assessed by MTT conversion assay.

In addition to the pools, clonal lines were derived from both MCF7 and BJAB transfectants and challenged by activation of the TNF and Fas death pathways. In the MCF-7 cell line, vector clones were uniformly sensitive to apoptosis induced by either TNF or anti-Fas+CHX, whereas among the transfected clones, those which expressed detectable crmA were totally resistant to apoptosis (FIG. 3A). Indeed, lines expressing the highest levels of crmA were totally resistant to apoptosis (FIG. 3A) and showed no morphologic cytopathic effects (FIG. 3B), demonstrating the crmA can completely block the TNF- and Fas-mediated death pathways. Similarly, among BJAB transfected clones, the crmA expressing the lines were markedly resistant to anti-Fas induced apoptosis whereas the vector clones were universally sensitive (FIG. 4A). Importantly, in both MCF7 and BJAB transfectants, those clones expressing the highest levels of crmA were the most resistant while those clones expressing little or undetectable levels were the most sensitive (FIG. 3A and FIG. 4A). Although direct visual quantitation of apoptotic nuclei is the preferable measure of apoptosis, comparable results were obtained when either an MTT-conversion based death assay (FIG. 3A insert and FIG. 4A inset) or crystal violet staining (FIG. 3C) was employed to assess cell survival.

Figure 4B:
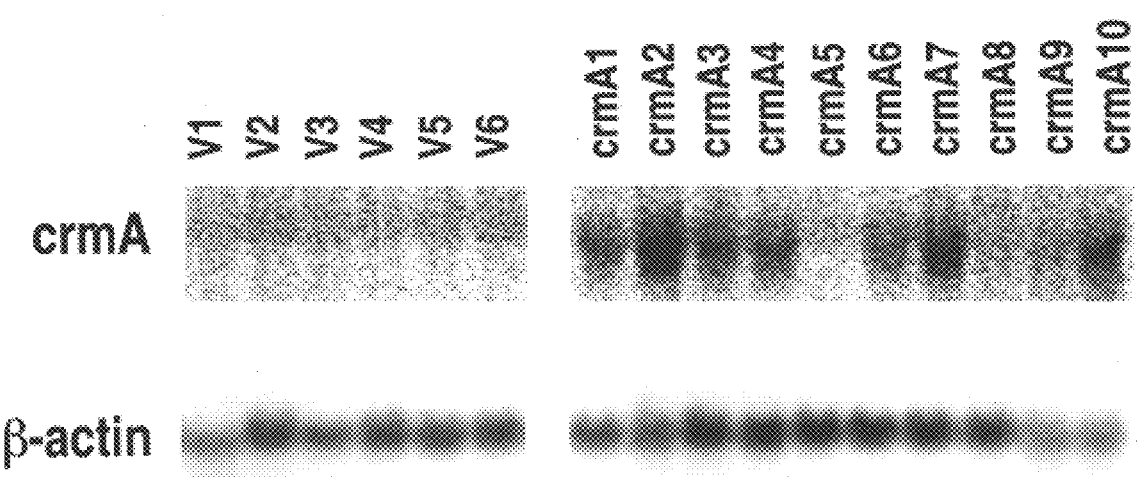
Figure 4C:
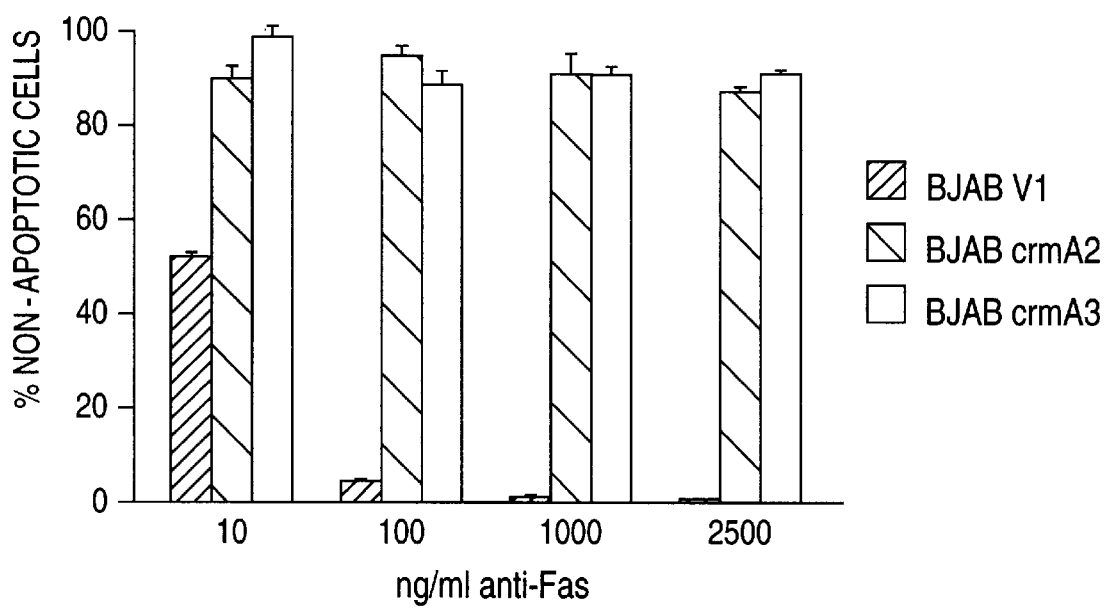
FIG. 4C shows crmA inhibits apoptosis by increasing doses of anti-Fas antibody. The acridine orange apoptosis assay was used to analyze the sensitivity of vector transfected (BJAB V1) or crmA-transfected (BJAB crmA2, BJAB crmA3) clones to apoptosis induced by the indicated doses of anti-Fas antibody.

The dose of death stimulus was increased to determine if protection conferred by crmA from cytokine-induced apoptosis could be attenuated. Remarkably, crmA afforded comparably high levels of protection from anti-Fas-induced apoptosis in response to doses of antibody 250 times greater than those needed to kill greater than 95% of the vector transfected cells (FIG. 4B). Similar results were obtained when the dose of TNF was similarly varied for the MCF7 transfectants, implying that crmA is functioning as an exceptionally potent inhibitor of cell death at a presumably critical step in the death pathway.

These results describe an important new function for crmA—the blockade of TNF- and Fas-mediated apoptosis. Given the importance of both TNF and Fas in the host anti-viral response, it is likely that this function of crmA is important for productive viral infection in vivo. crmA represents yet another example of viral economy in which two important functions, namely the inhibition of IL-1β production and the prevention of apoptosis, are embedded in one protein.

Additionally, this data have implications for the unification of death pathways in general. First, the fact that crmA blocks both TNF- and Fas-mediated apoptosis, especially in the MCF7 cells that possess both receptors, suggests that they signal death through a biochemically common pathway. This hypothesis is supported by the finding that the cytoplasmic regions of both these receptors encompass a region of homology which has been defined by mutational analysis as a "death domain" and which presumably interacts with a common set of signal transduction molecules. Further, it is not apparent that crmA blocks cell death triggered by two very different stimuli: growth factor withdrawal in neuronal cultures and, activation of cytokine receptors. It is of note that apoptosis in these two systems has been suggested to occur through biochemically distinct pathways, in that apoptosis in the former system is dependent on new protein synthesis and death is blocked by cycloheximide, whereas in contrast TNF- and Fas-mediated cytotoxicity is independent of new protein synthesis and is, in fact, enhanced by cycloheximide. Thus, at some point, the death pathway in both systems converges upon a crmA-inhibitable step, likely the activation of a protease.

Throughout this application, various publications are referred to by their bibliographical citation. The disclosures of these references are hereby incorporated by reference into this application to more fully describe the state of the art to which this invention pertains.

What is claimed is:

1. A method for preventing or inhibiting apoptosis, in a mammalian cell, wherein the cell is induced to apoptosis by the binding of a ligand to its cell surface receptor, comprising introducing into the mammalian cell an effective amount of a nucleic acid molecule coding for a gene product having crmA biological activity and under conditions such that apoptosis is prevented or inhibited.

2. The method of claim 1, wherein the mammalian cell has a receptor selected from the group consisting of a Fas receptor, a TNF receptor, a TCR, a CD4 receptor and a CD3 receptor.

3. The method of claim 2, wherein the cell is a CD4$^+$ T cell.

4. The method of claim 3, wherein the CD4$^+$ T cell contains a human immunodeficiency virus (HIV).

5. The method of claim 1, wherein the nucleic acid molecule is introduced into the mammalian cell in vitro.

6. The method of claim 1, wherein the nucleic acid molecule is introduced into the mammalian cell ex vivo.

7. The method of claim 1, wherein the nucleic acid molecule is introduced into the mammalian cell in vivo.

8. The method of claim 1, wherein the nucleic acid comprises DNA encoding poxvirus crmA or a DNA encoding a biologically active fragment of poxvirus crmA.

9. A method for maintaining T cell viability in a subject infected with the human immunodeficiency virus, comprising administering to the subject an effective amount of a nucleic acid molecule coding for a gene product having crmA biological activity and under conditions such that T cells remain viable.

10. The method of claim 9, wherein the subject is an animal.

11. The method of claim 9, wherein the subject is a human patient.

* * * * *